(12) United States Patent
Hesse et al.

(10) Patent No.: US 6,881,730 B1
(45) Date of Patent: Apr. 19, 2005

(54) STEROID COMPOUNDS WITH A C17-ALKYL SIDE CHAIN AND AN AROMATIC A-RING FOR USE IN THERAPY

(75) Inventors: Robert Henry Hesse, Winchester, MA (US); Sundara Katugam Srinivasasetty Setty, Cambridge, MA (US); Malathi Ramgopal, Andover, MA (US); Sanga Kugabalnsooriar, Burlington, MA (US)

(73) Assignee: Research Institute for Medicine & Chemistry, Inc., Cambridge, MA (US)

( * ) Notice: Subject to any disclaimer, the term of this patent is extended or adjusted under 35 U.S.C. 154(b) by 0 days.

(21) Appl. No.: 09/926,491

(22) PCT Filed: May 11, 2003

(86) PCT No.: PCT/GB00/01813

§ 371 (c)(1),
(2), (4) Date: Mar. 29, 2002

(87) PCT Pub. No.: WO00/68246

PCT Pub. Date: Nov. 16, 2000

(30) Foreign Application Priority Data

May 11, 1999 (GB) .............................................. 9910934

(51) Int. Cl.[7] .............................. A61K 31/56; C07J 9/00
(52) U.S. Cl. ........................ 514/182; 552/541; 552/544; 552/552
(58) Field of Search ................................. 514/182, 822, 514/825, 826, 841; 552/541, 544, 552

(56) References Cited

U.S. PATENT DOCUMENTS

| | | |
|---|---|---|
| 3,562,260 A | 2/1971 | de Ruggieri et al. |
| 3,717,627 A | 2/1973 | Laing S. et al. |

OTHER PUBLICATIONS

Dolence et al., "A stereoselective synthesis of 1,2–diols from .alpha.–hydroxyaldehydes", Tetrahedron Letters, vol. 26(9), 1189–1192, 1985.*

Dolence et al., "A Stereoselective synthesis of 1,2–diols from alpha–hydroxyaldehydes." Abstract from CASREACT, 1985.*

Chemical Abstracts, vol. 131, No. 8, Aug. 23, 1999, Columbus, Ohio, Abstract No. 97731, Mountford, Joanne C. et al., "Estrone potentiates myeloid cell differentiation: a role for 17.beta.–hydroxysteroid dehydrogenase in modulating hemopoiesis" XP002147254 Abstract & Exp. Hematol. (NY) 1999, 27(3), 451–460, (abstract only).

Chemical Abstracts, vol. 120, No. 23, Jun. 6, 1994, Columbus, Ohio, Abstract No. 290344, Lajeunesse, Daniel, "Effect of 17.beta.–estradiol on the human ostosarcoma cell line MG–63", XP002147255, Abstract & Bone Miner, 1994, 24(1), 1–16, (abstract only).

Chemical Abstracts, vol. 119, No. 7,. Aug. 16, 1993, Columbus, Ohio, Abstract No. 63468, Escaleira, Maria Teresa F. et al., "Sex steroids induced up–regulation of 1,25–dihydroxyvitamin D3 receptors in T 47D breast cancer cells", XP002147256, Abstract & J. Steroid Biochem. Mol. Biol., 1993, 45(4), 257–63, (abstract only).

Chemical Abstracts, vol. 116, No. 25, Jun. 22, 1992, Columbus, Ohio, Abstract No. 248829, Liel, Yair et al., "Evidence that estrogens modulate activity and increase the number of 1,25–dihydroxyvitamin D receptors in osteoblast–like cells (ROS 17/2.8)", XP002147257, Abstract & Endocrinology (Baltimore), 1992, 130(5), 2597–601, (abstract only).

* cited by examiner

*Primary Examiner*—Barbara P. Badio
(74) *Attorney, Agent, or Firm*—Bacon & Thomas PLLC

(57) ABSTRACT

Compounds of Formula (I) in which: $R^1$ and $R^2$, which may be the same or different, each represents a lower alkyl, alkenyl or alkynyl group; $R^3$ represents a methyl group having α- or β-configuration; $R^4$ represents a hydrogen atom or an etherifying or esterifying group; $R^5$ represents a hydrogen atom, a hydroxyl group or a lower alkoxy group; X represents a group $OR^4$, wherein $R^4$ is as defined above, or a group $NR^6R^7$ wherein $R^6$ represents a hydrogen atom, an aliphatic or araliphatic organic group, or an acyl group comprising an aliphatic, araliphatic or aryl organic group linked to the nitrogen atom by way of a carbonyl group; and $R^7$ is a hydrogen atom or a lower alkyl group; Y represents a lower alkylene, alkenylene or alkynylene group optionally substituted by a hydroxyl, etherified hydroxyl or esterified hydroxyl group; and the dotted lines signify that double bonds may be present at the 16(17)-position and/or either at the 6(7)- and 8(9)-positions or at the 7(8)-position exhibit potent effects on modulation of cell growth and differentiation, while having low calcaemic activity.

18 Claims, No Drawings

STEROID COMPOUNDS WITH A C17-ALKYL SIDE CHAIN AND AN AROMATIC A-RING FOR USE IN THERAPY

This invention relates to novel sterol derivatives, more particularly to ring A aromatic sterol derivatives in which the 17-position side chain terminates in an amino, amido or hydroxyl group and which exhibit cell modulating activity.

It is well known that 9,10-seco sterol derivatives such as vitamin $D_3$ play a vital role in the metabolism of calcium by promoting intestinal absorption of calcium and phosphorus, maintaining adequate serum levels of calcium and phosphorus, and stimulating mobilisation of calcium from the bone fluid compartment in the presence of parathyroid hormone. Following the discovery that D vitamins are hydroxylated in vivo, at the 25-position in the liver and at the 1α-position in the kidneys, and that the resulting 1α,25-dihydroxy metabolite is the biologically active material, extensive studies have been carried out on vitamin D analogues hydroxylated at, for example, the 1α- and 24R- or 25-positions.

The natural metabolite 1α,25-dihydroxy vitamin $D_3$ has additionally been found to have effects on cellular metabolism, these cell modulating effects including stimulation of cell maturation and differentiation, immunosuppressive effects and immunopotentiating effects (e.g. by stimulating the production of bactericidal oxygen metabolites and the chemotactic response of leukocytes). However, the potent effects of compounds such as 1α,25-dihydroxy vitamin $D_3$ on calcium metabolism will normally preclude their use in this area, since doses sufficient to elicit a desired cell modulating effect will tend to lead to unacceptable hypercalcaemia.

This has led to attempts to synthesize new vitamin D analogues which have reduced effects on calcium metabolism but which still exhibit the desired effects on cellular metabolism. Representative examples of such analogues, together with summaries of earlier attempts to solve this problem, are given in WO-A-9309093, WO-A-9426707, WO-A-9525718 and WO-A-9516672, the contents of which are incorporated herein by reference.

It is currently believed that such vitamin D analogues act as general regulators of cell growth and differentiation through receptor-mediated (especially nuclear receptor-mediated) processes involving modulation of vitamin D responsive genes (M. R. Waters, Endoc. Rev. 13, pp. 719–764 [1992]). It has also hitherto been assumed that the seco steroid 5,7,10(19)-triene system or a similar 19-nor seco steroid 5,7-diene system is a prerequisite for any form of cell modulating activity. Thus, whilst workers investigating vitamin D analogues have modified the A-ring and 17-position side chain and in certain cases have made more drastic modifications to the overall molecular skeleton such as modification or even elimination of the C- and/or D-rings, they have attempted to retain the triene or conjugated diene system (Gui-Dong Zhu et al., Bioorganic & Med. Chem. Lett. 6, pp. 1703–1708 [1996]; K. Sabbe et al., Bioorganic & Med. Chem. Lett. 6, pp. 1697–1702 [1996]).

Workers have recently reported the observation of non-genomic rapid responses to vitamin D analogues which they attribute to interaction with a putative cell membrane-located vitamin D receptor (A. W. Norman et al., J. Steroid Biochem. and Mol. Biol. 56, pp. 13–22 [1996]). It has also been reported that such non-genomic rapid effects may be elicited by 1α,3β,25-trihydroxycholesta-5,7-diene, i.e. the pro-vitamin form of 1α,25-dihydroxy vitamin $D_3$, which is not a seco steroid; this has been attributed to the ability of the pro-vitamin to mimic the 6,7-s-cis conformation of the normal vitamin D triene (Norman, op. cit.). However, the pro-vitamin has been reported to have little ability to elicit the genomic effect believed to underlie modulation of cell growth and differentiation (Norman, op. cit.) and has also been reported not to exhibit the typical effects of vitamin D on skin (R. Gniadecki et al., British J. Dermatol. 132, pp. 841–852 [1995]).

The present invention is based on the surprising finding that a range of simple sterol derivatives which have an intact tetracyclic nucleus and lack both the seco steroid triene system of vitamin D analogues and the ability to mimic a conjugated conformational isomer thereof, exhibit potent effects on the modulation of cell growth and differentiation, for example as demonstrated by their ability to inhibit growth of cancer cells in vitro and in vivo, and their ability to promote the healing of ear punches in vivo. The compounds possess an advantageous therapeutic ratio by virtue of their low levels of calcaemic activity, for example as determined by their effects on serum calcium and phosphorus levels in rats.

The compounds of the invention comprise 3-sterols (and O-protected derivatives thereof) having an aromatic A ring and an amine-, amide- or hydroxyl-terminated 17-position side chain. The compounds may also contain an aromatic B-ring or a double bond at the 7(8)-position and/or a double bond at the 16(17)-position.

Thus according to one embodiment of the invention there are provided compounds of formula (I)

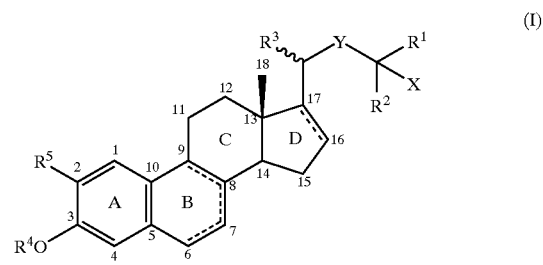

in which:
R$^1$ and R$^2$, which may be the same or different, each represents a lower alkyl, alkenyl or alkynyl group;
R$^3$ represents a methyl group having α- or β-configuration;
R$^4$ represents a hydrogen atom or an etherifying or esterifying group;
R$^5$ represents a hydrogen atom, a hydroxyl group or a lower alkoxy group;
X represents a group OR$^4$, wherein R$^4$ is as defined above, or a group NR$^6$R$^7$ wherein R$^6$ represents a hydrogen atom, an aliphatic or araliphatic organic group, or an acyl group comprising an aliphatic, araliphatic or aryl organic group linked to the nitrogen atom by way of a carbonyl group; and R$^7$ is a hydrogen atom or a lower alkyl group;
Y represents a lower alkylene, alkenylene or alkynylene group optionally substituted by a hydroxyl, etherified hydroxyl or esterified hydroxyl group; and
the dotted lines signify that double bonds may be present at the 16(17)-position and/or either at the 6(7)- and 8(9)-positions or at the 7(8)-position.

R$^1$ and R$^2$ may, for example, be selected from lower (e.g. $C_{1-6}$) alkyl groups such as methyl, ethyl, propyl and butyl groups, lower (e.g. $C_{2-7}$) alkenyl groups such as allyl, and lower (e.g. $C_{2-7}$) alkynyl groups such as propargyl. Where appropriate the groups may be straight chain or branched; straight chain groups may be preferred.

Where $R^3$ in formula (I) is a methyl group in the α-configuration, the compounds have the 20R configuration characteristic of natural sterols such as cholesterol; where $R^3$ is in the β-configuration the compounds have the 20S configuration of the corresponding epi-derivatives. It will be appreciated that the invention also embraces mixtures of the two isomers.

Where $R^4$ represents an etherifying or an esterifying group this may, for example, comprise any suitable cleavable O-protecting group such as is commonly known in the art. Such O-protected derivatives of compounds of formula (I) are useful in the preparation of active compounds (I) in which $R^4$ represents a hydroxy group and may also, where the O-protecting group is either metabolically labile in vivo or is a lower alkyl etherifying group such as methyl, ethyl or isobutyl, be useful directly in therapy. Representative O-protecting groups include (i) etherifying groups such as silyl groups (e.g. tri(lower alkyl)silyl groups such as trimethylsilyl, triethylsilyl, triisopropylsilyl or t-butyldimethylsilyl; tri(aryl)silyl groups such as triphenylsilyl; and mixed alkyl-arylsilyl groups), lower (e.g. $C_{1-6}$) alkyl groups optionally interrupted by one or more oxygen atoms (e.g. such as methyl, ethyl methoxymethyl or methoxyethoxymethyl) or substituted by a lower (e.g. $C_{2-8}$) cycloalkyl group (e.g. as in cyclopentylmethyl), and cyclic ether groups (e.g. such as tetrahydropyranyl), and (ii) esterifying groups such as lower (e.g. $C_{1-6}$) alkanoyl (e.g. such as acetyl, propionyl, isobutyryl or pivaloyl), aroyl (e.g. containing 7–15 carbon atoms, such as benzoyl or 4-phenylazobenzoyl), lower (e.g. $C_{1-6}$) alkane sulphonyl (e.g. such as methane sulphonyl or halogenated methane sulphonyl) and arene sulphonyl (e.g. such as p-toluene sulphonyl). Where appropriate the groups may be straight chain or branched.

Where $R^5$ represents a lower alkoxy group, this may for example be a straight chain or branched $C_{1-6}$ alkoxy group such as a methoxy, ethoxy or propoxy group.

Where $R^6$ represents an aliphatic group this may, for example, be a lower alkyl group, for example a straight chain $C_{1-6}$ alkyl group such as a methyl, ethyl, propyl or butyl group. Araliphatic groups $R^6$ may, for example, include $C_{6-12}$ carbocyclic aryl $C_{1-4}$ alkyl groups such as benzyl or phenethyl. Where $R^6$ represents an acyl group this may, for example, be a lower (e.g. $C_{1-6}$) alkanoyl group such as formyl, acetyl or propionyl; a $C_{6-12}$ carbocyclic aryl $C_{2-5}$ alkanoyl group such as phenylacetyl; or a $C_{7-13}$ carbocyclic aroyl group such as benzoyl. The group $R^6$ may optionally carry one or more substituents, for example selected from halo (e.g. chloro or bromo), lower (e.g. $C_{1-4}$) alkyl such as methyl, lower alkoxy (e.g. methoxy), lower alkanoyl (e.g. acetyl), lower alkylamino (e.g. methylamino), di(lower alkyl)amino (e.g. dimethylamino), nitro, carbamoyl and lower alkanoylamino (e.g. acetamido).

When $R^7$ represents a lower alkyl group, this may, for example, be a straight chain or branched $C_{1-6}$ alkyl group such as a methyl, ethyl, propyl or butyl group.

Lower alkylene, alkenylene or alkynylene groups represented by Y may, for example, contain up to 7 carbon atoms and up to 3 multiple bonds. Y may advantageously be a straight chain group, e.g. containing 2–6 carbon atoms, for example as in ethylene, trimethylene, tetramethylene, pentamethylene, hexamethylene, vinylene, buta-1,3-dienylene, propynylene (e.g. prop-2-ynylene), but-1-ynylene or but-2-ynylene.

Where Y is substituted by a hydroxyl, etherified hydroxyl or esterified hydroxyl group, this substituent may advantageously be positioned α-, β- or γ- to the group —$C(R^1)(R^2)$.X or α- to any triple bond present in the group Y, e.g. as in 1-hydroxyprop-2-ynylene. Etherifying groups which may be present include lower (e.g. $C_{1-6}$) alkyl groups optionally interrupted by one or more oxygen atoms (e.g. methyl, methoxymethyl or methoxyethoxymethyl), and cyclic groups such as tetrahydropyranyl. Esterifying groups which may be present include lower (e.g. $C_{1-6}$) alkanoyl such as acetyl, propionyl, isobutyryl or pivaloyl; lower alkenoyl (e.g. allylcarbonyl); aroyl (e.g. p-nitrobenzoyl); lower alkoxycarbonyl (e.g. t-butoxycarbonyl); lower haloalkoxycarbonyl (e.g. 2,2,2-trichloroethoxycarbonyl or 1,1,1-trichloro-2-methyl-2-propoxycarbonyl); aralkyloxycarbonyl (e.g. benzyloxycarbonyl or p-nitrobenzyloxycarbonyl); and lower alkenyloxycarbonyl (e.g. allyloxycarbonyl). It will be appreciated that it may be advantageous to select etherifying or esterifying groups which are metabolically labile in vivo.

The cell modulating activity of compounds according to the invention, including O-protected derivatives in which the O-protecting group is metabolically labile, combined with their substantial lack of calcaemic effect, render them of interest both alone and as adjuncts in the management of diseases associated with abnormal cell proliferation, such as neoplastic disease, particularly myelogenous leukemias as well as neoplastic disease of the brain, breast, stomach, gastrointestinal tract, prostate, pancreas, uro-genital tract (male and female) and pulmonary neoplasia. Their ability to promote closure of mouse ear punches suggests their use, either alone or as adjuncts, as agents to promote wound healing. Compounds of the invention also appear to promote healing of experimental burns, suggesting a utility in burn management. The cell modulating activity of compounds of the invention suggests that they may, like vitamin D analogues, have additional utilities either alone or as adjuncts in the chemotherapy of infection and in other therapeutic modalities in which mononuclear phagocytes are involved, for example in treatment of bone disease (e.g. osteoporosis, osteopenia and osteodystrophy as in rickets or renal osteodystrophy), autoimmune disease, host-graft reaction, transplant rejection, inflammatory diseases (including modulation of immunoinflammatory reactions), neoplasias and hyperplasias, myopathy, enteropathy and spondylitic heart disease, their potential utility in treatment of neoplasias and hyperplasias being evidenced by their ability to inhibit human cancer xenografts in severe combined immunodeficiency mice. Additionally, they may be useful in suppression of parathyroid hormone (e.g. as in serum calcium homeostasis), in treatment of dermatological diseases (for example including acne, alopecia, eczema, pruritus, psoriasis and skin aging, including photoaging), hypertension, rheumatoid arthritis, psoriatic arthritis, secondary hyperparathyroidism, asthma, cognitive impairment and senile dementia (including Alzheimer's disease), in fertility control in both human and animal subjects, and in management of disorders involving blood clotting (e.g. by dissolution of existing clots and/or by prevention of clotting). The invention embraces use of these compounds in the therapy or prophylaxis of such conditions and in the manufacture of medicaments for use in such treatment or prophylaxis.

Compounds of the invention have also been found to bind to oestrogen receptors, whilst being free from and even inhibiting uterotrophic effects such as are associated with conventional oestrogens. This binding effect, in combination with their anabolic wound healing effects, suggests that such compounds may additionally be useful in prevention or treatment of osteoporosis and in reduction of serum cholesterol.

Active compounds according to the invention may be formulated for administration by any convenient route, e.g. orally (including sublingually), parenterally, rectally or by inhalation; pharmaceutical compositions so formulated comprise a feature of the invention.

Orally administrable compositions may, if desired, contain one or more physiologically compatible carriers and/or excipients and may be solid or liquid. The compositions may take any convenient form including, for example, tablets, coated tablets, capsules, lozenges, aqueous or oily suspensions, solutions, emulsions, syrups, elixirs and dry products suitable for reconstitution with water or another suitable liquid vehicle before use. The compositions may advantageously be prepared in dosage unit form. Tablets and capsules according to the invention may, if desired, contain conventional ingredients such as binding agents, for example syrup, acacia, gelatin, sorbitol, tragacanth or polyvinyl-pyrrollidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. Tablets may be coated according to methods well known in the art.

Liquid compositions may contain conventional additives such as suspending agents, for example sorbitol syrup, methyl cellulose, glucose/sugar syrup, gelatin, hydroxymethylcellulose, carboxymethylcellulose, aluminium stearate gel or hydrogenated edible fats; emulsifying agents, for example lecithin, sorbitan monooleate or acacia; non-aqueous vehicles, which may include edible oils, for example vegetable oils such as arachis oil, almond oil, fractionated coconut oil, fish-liver oils, oily esters such as polysorbate 80, propylene glycol, or ethyl alcohol; and preservatives, for example methyl or propyl p-hydroxybenzoates or sorbic acid. Liquid compositions may conveniently be encapsulated in, for example, gelatin to give a product in dosage unit form.

Compositions for parenteral administration may be formulated using an injectable liquid carrier such as sterile pyrogen-free water, sterile peroxide-free ethyl oleate, dehydrated alcohol or propylene glycol or a dehydrated alcohol/propylene glycol mixture, and may be injected intravenously, intraperitoneally or intramuscularly.

Compositions for rectal administration may be formulated using a conventional suppository base such as cocoa butter or another glyceride.

Compositions for administration by inhalation are conveniently formulated for self-propelled delivery, e.g. in metered dose form, for example as a suspension in a propellant such as a halogenated hydrocarbon filled into an aerosol container provided with a metering dispense valve.

It may be advantageous to incorporate an antioxidant, for example ascorbic acid, butylated hydroxyanisole or hydroquinone in the compositions of the invention to enhance their storage life.

Where any of the above compositions are prepared in dosage unit form these may for example contain 10 µg –100 mg, preferably 100 µg –100 mg of active compound according to the invention per unit dosage form; such dosage units may for example be administered 1–4 times per day. The compositions may if desired incorporate one or more further active ingredients.

A suitable daily dose of an active compound according to the invention may for example be in the range 100 µg –400 mg, per day, depending on factors such as the severity of the condition being treated and the age, weight and condition of the subject.

Compounds according to the invention may be prepared by any convenient method, for example by reaction of a compound containing a precursor for the desired 17-position side chain in one or more stages and with one or more reactants serving to form the said desired 17-position side chain, followed if necessary and/or desired by removal of any O-protecting group.

Appropriate techniques for formation of a desired side chain include those described in the aforementioned WO-A-9516672.

Thus, for example, in order to prepare a compound (I) in which $R^1$ and $R^2$ are identical and X is the group $NR^6R^7$ in which $R^6$ and $R^7$ are hydrogen atoms, a compound of general formula (II)

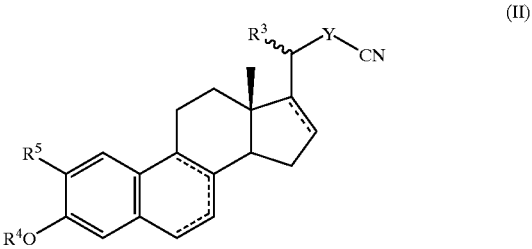

(II)

(where $R^3$, $R^4$, $R^5$ and Y are as hereinbefore defined) may be reacted with an organo-cerium reagent, e.g. prepared in situ from cerous chloride and an appropriate organometallic compound, e.g. an alkyl/cycloalkyl lithium compound of formula $R^1Li$ (where $R^1$ is as hereinbefore defined), for example as described by Ciganek (J. Org. Chem. 57, pp. 4521–4527 [1992]).

Compounds of formula (I) in which $R^1$ and $R^2$ are different and X is the group $NR^6R^7$ in which $R^6$ and $R^7$ are hydrogen atoms may, for example, be prepared by reacting a thio-oxime of formula (III)

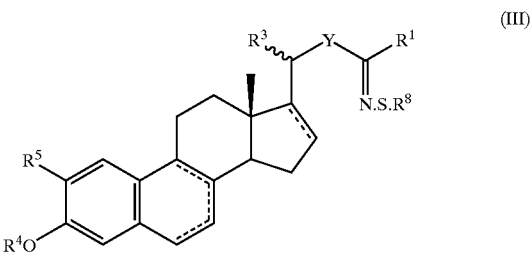

(III)

(where $R^1$, $R^3$, $R^4$, $R^5$ and Y are as hereinbefore defined and $R^8$ is an aromatic group, e.g. a carbocyclic aryl group such as phenyl) with an appropriate organometallic compound, for example an alkyl/cycloalkyl lithium compound of formula $R^2Li$ (where $R^2$ is as hereinbefore defined), and reducing the thus-obtained compound of formula (IV)

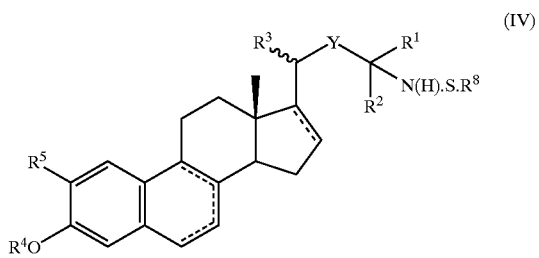

(IV)

(where $R^1$, $R^2$, $R^3$, $R^4$, $R^5$, $R^8$ and Y are as hereinbefore defined), e.g. using a metal hydride reducing agent such as sodium borohyride or an inorganic or organic sulphur compound such as hydrogen sulphide, sodium sulphide or a thiol (e.g. a lower alkyl mercaptan such as methanethiol) to remove the $R^8$.S group and yield a corresponding compound of formula (I) in which X is the group $NR^6R^7$ in which $R^6$ and $R^7$ represent hydrogen atoms (see J. Org. Chem. 42, pp. 398–399 [1977]).

Compounds of formula (I) where X is a group $NR^6R^7$ in which $R^6$ represents a lower alkanoyl, aralkanoyl or aroyl group and $R^7$ represents a hydrogen atom may be prepared by acylation of a corresponding compound (I) in which $R^6$ is hydrogen, for example by reaction with an appropriate acyl halide or acid anhydride, preferably in the presence of water or a lower alcohol, as may typically be incorporated to suppress acylation of groups other than the amino group, or with an appropriate acid in the presence of a coupling agent such as N,N'-carbonyl-diimidazole or dicyclohexylcarbodiimide. It will be appreciated that if the acylation is carried out in the absence of components such as water or lower alcohols which suppress the acylation of hydroxyl groups, then any hydroxyl groups present in the molecule, e.g. at the 2- or 3-position or as a substituent of the Y group, should desirably be in O-protected form during such an acylation reaction.

Compounds of formula (I) where X is a group $NR^6R^7$ in which $R^6$ represents an aliphatic or araliphatic group and $R^7$ represents a hydrogen atom may, for example, be prepared by reducing a corresponding compound (I) in which $R^6$ is an aliphatic or araliphatic acyl group, e.g. using a metal hydride reducing agent such as lithium aluminium hydride.

Compounds of formula (I) where X is a group $NR^6R^7$ in which at least one of $R^6$ and $R^7$ represents a hydrogen atom may be subjected to appropriate substitution reactions to introduce desired $R^6$ and/or $R^7$ groups, for example to direct alkylation, e.g. by reaction with an alkyl halide, or to reductive amination, e.g. by reaction with an appropriate aldehyde and a reducing agent such as sodium cyanoborohydride.

Compounds of formula (I) in which X is a hydroxyl group may, for example, be prepared by reaction of a compound of formula (V)

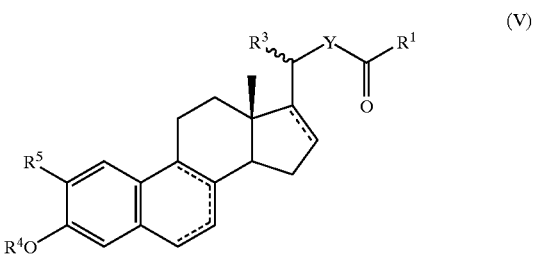

(V)

(where $R^1$, $R^3$, $R^4$, $R^5$ and Y are as hereinbefore defined) with an appropriate organometallic compound, for example a compound of formula $R^2Li$ (where $R^2$ is as hereinbefore defined).

Compounds of formula (I) in which X is a hydroxyl group and $R^1$ and $R^2$ are identical may similarly be prepared by reaction of a compound of formula (VI)

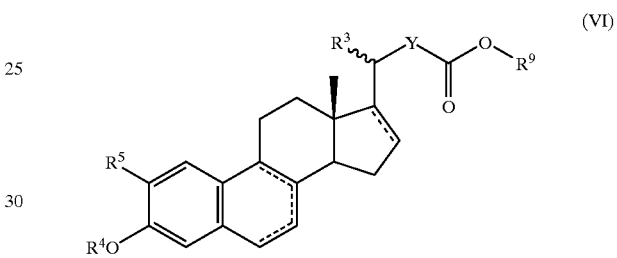

(VI)

(where $R^3$, $R^4$, $R^5$ and Y are as hereinbefore defined and $R^9$ is a lower [e.g. $C_{1-6}$] alkyl group such as methyl, ethyl, isopropyl or isoamyl) with an excess of an appropriate organometallic compound, for example a compound of formula $R^1Li$ (where $R^1$ is as hereinbefore defined and is identical to $R^2$).

Compounds of formula (I) in which Y is an alkynylene group may, for example, be prepared by reaction of a compound of formula (VII)

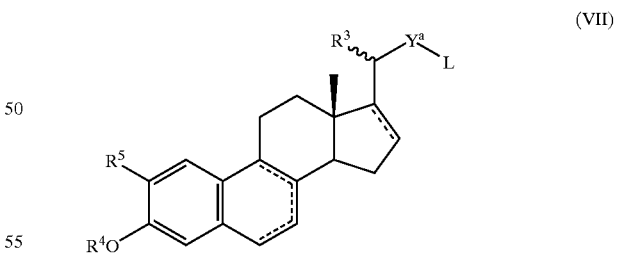

(VII)

(where $R^3$, $R^4$ and $R^5$ are as hereinbefore defined; $Y^a$ is an alkylene group, e.g. containing 1–4 carbon atoms; and L represents a leaving group, for example a sulphonate ester group, e.g. lower alkyl sulphonyloxy such as mesyloxy, lower fluoroalkyl sulphonyloxy such as trifluoromethanesulphonyloxy or aryl sulphonyloxy such as tosyloxy, or a halogen atom such as chlorine, bromine or iodine), with a metallated derivative (e.g. the lithio derivative) of an alkyne of formula (VIII)

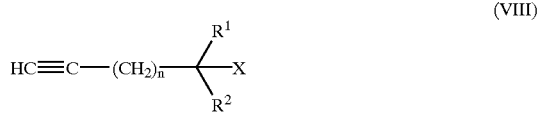

(VIII)

(where $R^1$, $R^2$ and X are as hereinbefore defined and n is 0 or an integer, e.g. in the range 1–3).

The thus obtained compound (I) in which Y is the group

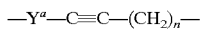

(wherein $Y^a$ and n are as hereinbefore defined) may if desired be hydrogenated to convert the triple bond either to a double bond (e.g. using Lindlar catalyst) or to a single bond (e.g. using a noble metal catalyst such as platinum, palladium or homogeneous rhodium or ruthenium).

Compounds of formula (I) in which Y is an alkynylene group carrying a hydroxyl group a to the triple bond may, for example, be prepared by reaction of a compound of formula (IX)

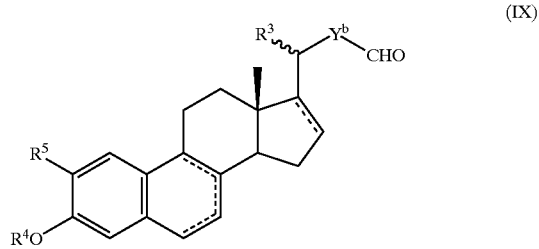

(IX)

(where $R^3$, $R^4$ and $R^5$ are as hereinbefore defined and $Y^b$ is a valence bond or an alkylene group, e.g. containing 1–4 carbon atoms) with a metallated derivative of an alkyne of formula (VIII), so as to form a compound (I) in which Y is a group

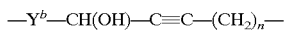

(wherein $Y^b$ and n are as hereinbefore defined).

Compounds of formula (VIII) may be prepared by subjecting a compound of formula (X)

 (X)

(where n, $R^1$ and $R^2$ are as hereinbefore defined) to a Ritter reaction with a compound of formula $R^a$CN (where $R^a$ represents a hydrogen atom or an appropriate organic group) in the presence of a strong acid, e.g. a mineral acid such as sulphuric acid, thereby leading to formation of a compound (I) where X is the group $NR^6R^7$ in which $R^6$ represents a group $R^a$.CO— and $R^7$ is a hydrogen atom. The $R^6$ group may be removed by hydrolysis to yield a compound (I) in which $R^6$ represents a hydrogen atom or may be reduced, e.g. as hereinbefore described, to yield a compound (I) in which $R^6$ represents a group $R^a$.$CH_2$—. Alternatively the hydroxyl group of the tertiary carbinol may be displaced by an azido group, e.g. by reaction with hydrazoic acid in the presence of a strong acid, and the azido group reduced to yield a compound (I) where X is the group $NR^6R^7$ in which $R^6$ and $R^7$ represent hydrogen atoms. The internal alkyne group may then be isomerized to the terminal position by treatment with the potassium salt of 1,3-propanediamine in 1,3-propanediamine as solvent ("acetylene zipper").

Compounds of formula (II) may, for example, themselves be prepared by reaction of a compound of formula (VII) as defined above with, as appropriate, (i) a source of cyanide ion (e.g. an alkali metal cyanide such as sodium or potassium cyanide), (ii) a metallated acetonitrile derivative (e.g. the lithio derivative), or (iii) acrylonitrile, preferably where L is an iodine atom (e.g. by ultrasound-induced chromium-mediated conjugate addition as described by Mourino et al. in J. Org. Chem. 58, pp. 118–123 [1993]).

Compounds (II) in which the 17-position side chain terminates in the group —CH:CH.CN may, for example, be prepared from an aldehyde of formula (IX) as defined above by means of a Wittig reaction with an ylid of formula $(R^{10})_3$P:CH.CN (where each $R^{10}$ represents an organic group, e.g. a carbocyclic aryl group such as phenyl) or with a corresponding phosphonate or silyl equivalent.

Compounds of formula (III) may, for example, themselves be prepared by reacting a ketone of formula (V) with an S-substituted thiolamine of formula $R^8$.S.NH (where $R^8$ is as hereinbefore defined). Such compounds of formula (V) may, for example, be prepared from an acid of formula (XI)

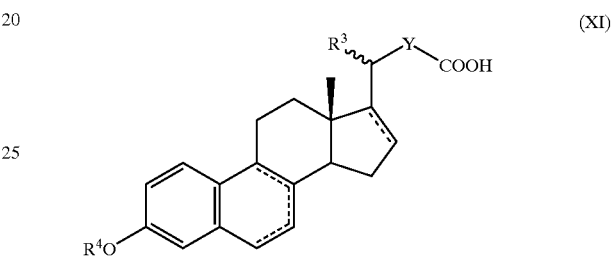

(XI)

(where $R^3$, $R^4$, $R^5$ and Y are as hereinbefore defined), e.g. by formation of a corresponding acid halide such as the chloride and reaction with an organometallic compound $R^1MX$ (where $R^1$ is as hereinbefore defined; M represents a divalent metal such as copper, zinc or cadmium; and X represents e.g. a halogen atom). Alternatively one may prepare compounds (V) by reacting a compound of formula (VII) above with e.g. (i) an α-metallated derivative such as a lithio derivative of a ketone of formula $CH_3$.CO.$R^1$ (where $R^1$ is as hereinbefore defined) or with a corresponding enol, or (ii), preferably where L is an iodine atom, a vinyl ketone of formula $CH_2$:CH.CO.$R^1$ (where $R^1$ is as hereinbefore defined), e.g. by ultrasound-induced chromium-mediated conjugate addition as described by Mourino et al. (op. cit.).

Compounds (XI) and esters thereof, e.g. compounds of formula (VI), may also be used to prepare compounds of formula (II) by reaction with ammonia or a metallated derivative thereof, e.g. an alkali metal amide such as lithium amide, to form a corresponding carboxamide which may be converted to a nitrile (II) by mild dehydration, e.g. using tosyl chloride, phosphorus oxychloride in the presence of a base such as pyridine, or trifluoracetic anhydride in the presence of an excess of a base such as pyridine.

Compounds (II) in which Y is α-substituted by a hydroxyl group are conveniently obtained by cyanohydrin formation, for example by reaction of a compound (IX) with hydrogen cyanide. Compounds (II) in which Y is β-substituted by a hydroxyl group may be prepared directly by reaction of a compound (IX) with a metallated (e.g. lithiated) derivative of acetonitrile; they may also be prepared indirectly by reaction with a metallated derivative of an ester of acetic acid, followed by conversion of the ester group to a carboxamide group and then to a nitrile group, e.g. as described above.

In general compounds (I) and starting materials therefor in which Y is substituted by a hydroxyl group may be converted to corresponding ether and ester derivatives by standard methods such as are well known in the art. Thus, for example, etherification may be effected by reaction with an appropriate organic halide (e.g. an alkyl iodide) in the presence of an appropriate base (e.g. an alkali metal alkoxide such as potassium t-butoxide), advantageously in the presence of a crown ether such as 18-crown-6. Esterification may be effected by reaction with appropriate acylating agents, such as acyl halides, acid anhydrides and the like.

Compounds of formula (VII) may be prepared from estrone, equilenin or equilin as appropriate by, for example, Wittig reaction with an ethylidene phosphorane to convert the 17-one to the corresponding Z-17(20) ethylidene compound, following the procedure described by Krubiner and Oliveto, J. Org. Chem. 31, pp. 24–26 [1965]. Alternatively, the corresponding E-isomer may be obtained following the procedure of Midland and Kwon, Tetrahedron Lett. 23(20), pp. 2077–2080 [1982]. The thus-obtained alkenes may be subjected to conventional stereospecific hydroboration reactions followed by oxidative work-up with alkaline hydrogen peroxide solution (Krubiner, op. cit.) to afford the corresponding 20-ols, which may be oxidised to 20-ones with chromium trioxide (Krubiner, op. cit.). Wittig reaction with methoxymethylenetriphenylphosphorane, hydrolysis of the enol ether with aqueous acid (to give a non-stereospecific aldehyde of formula (IX) in which $Y^b$ represents a valence bond), reduction with sodium borohydride and reaction of the resulting alcohol with tosyl chloride affords compounds of formula (VII) wherein $R^3$ is methyl, $Y^a$ is methylene and L is tosyloxy.

Compounds of formula (VII) having a double bond at the 16(17)-position may, for example, be prepared stereospecifically by subjecting the appropriate E- or Z-17(20) ethylidene compound prepared as described above to a stereospecific ene reaction. For example, such ene reactions include treatment with formaldehyde, boron trifluoride and optionally acetic anhydride (Batcho et al., Helv. Chim. Acta 64, pp. 1682–1687 [1981]) to form compounds of formula (VII) in which $R^3$ is methyl, $Y^a$ is methylene and L is hydroxy or acetoxy. The acetyl group may be removed by hydrolysis and the hydroxyl group may be tosylated to generate a compound (VII) in which L is a suitable leaving group. In an alternative ene reaction, treatment with ethyl propiolate/diethyl aluminium chloride (Dauben and Brookhart, J. Am. Chem. Soc. 103, pp. 237–238 [1980]) affords ethyl esters of Δ16,17 acids of general formula (XI) in which $R^3$ is methyl and Y is ethylene, from which the corresponding free acid may be obtained by hydrolysis. The Δ16,17 compounds described above may be stereospecifically hydrogenated.

Compounds of formula (VII) in which $Y^a$ is e.g. ethylene or trimethylene may, for example, be obtained by reaction of a compound (VII) in which $Y^a$ is methylene either (i) with a reagent serving to introduce a one-carbon fragment (e.g. a metal cyanide) and conversion of the group so introduced to a group —$CH_2L$, e.g. by hydrolysing a cyano group to yield a carboxy group or by reducing such a cyano group (e.g. with a metal hydride reducing agent such as diisobutyl aluminium hydride) to yield a carboxaldehyde group, and reducing the carboxy or carboxaldehyde group (e.g. using sodium borohydride or lithium aluminium hydride) to yield a hydroxymethyl group which may in turn be subjected to tosylation and, if desired, nucleophilic displacement as hereinbefore described to effect conversion to a halomethyl group; or (ii) with a metallated derivative of an ester or thioester of acetic acid, with a derivative containing another carbanionic equivalent of acetic acid (e.g. a metallated derivative of acetonitrile), or with a metallated malonate ester (in which last instance the reaction product is partially hydrolysed to yield a monoester which may be decarboxylated by heating to yield a carboxylate ester), reducing the resulting ester or thioester product to an alcohol (e.g. using lithium aluminium hydride), and converting the resulting hydroxyl group to a leaving group, such as a tosylate group or a halogen atom, e.g. as hereinbefore described.

It will be appreciated that the above procedures (i) and/or (ii) may be repeated as needed to yield compounds (VII) in which $Y^a$ is a $C_{3-7}$ alkylene group.

In general, O-protecting groups may, for example, be removed by conventional methods such as are well documented in the literature. Thus esterifying acyl groups may be removed by basic hydrolysis, e.g. using an alkali metal alkoxide in an alkanol. Etherifying groups such as silyl groups may be removed by acid hydrolysis or treatment with a fluoride salt, e.g. a tetraalkyl ammonium fluoride. The use of such acid-labile but base-stable protecting groups may be of particular advantage during homologation steps to build up a desired side chain, in view of the strongly basic conditions normally employed for such reactions.

The following non-limitative examples serve to illustrate the invention. All temperatures are in °C.

Preparation 1 a) 3-Triisopropylsilyloxy-19-nor-chol-1,3,5(10),16-tetraen-24-ol [Formula (VII): $R^3$=α-$CH_3$, $R^4$=(i—Pr)$_3$Si, $R^5$=H, $Y^a$=($CH_2$)$_3$, L=OH, Δ16 double bond]

A solution of 3-triisopropylsilyloxy-19-nor-chol-1,3,5 (10),16,22-pentaene-24-carboxylic acid methyl ester [Formula (VII)—$R^3$=α-$CH_3$, $R^4$=(i-Pr)$_3$Si, $Y^a$=—CH=CH—, L=CO.O$CH_3$, Δ16 double bond] (177 mg—prepared by silylation of the corresponding 3-hydroxy compound) in ether (6.5 ml) was added dropwise to a solution of lithium aluminium hydride in ether (3 ml of a 1M solution). The mixture was stirred for 3 hours and worked up to afford the title compound as an approximately 85/15 mixture with the corresponding Δ22 compound.

b) 3-Triisopropylsilyloxy-19-nor-chol-1,3,5(10),16-tetraen-24-ol, 24-tosylate [Formula (VII): $R^3$=α-$CH_3$, $R^4$=(i-Pr)$_3$Si, $R^5$=H, $Y^a$=($CH_2$)$_3$, L=O,S$O_2$, $C_6H_4$,$CH_3$, Δ16 double bond]

A solution containing the mixture of alcohols from (a) above (223 mg), tosyl chloride (216 mg) and pyridine (476 μl) in methylene chloride (4 ml) was stirred at room temperature for 4 hours, treated with aqueous sodium bicarbonate solution, stirred overnight, and worked up to afford a mixture of the Δ22 alcohol and the title compound (190 mg): NMR (CDCl$_3$) δ 0.85 (s, 18-H's), 2.65 (s, tosyl-Me), 3.9 (t, 24-H's), 5.1 (bs, 16-H), 6.5 and 6.95 (m, 1-, 2- and 4-H's), 7.65 and 7.62 (ABq, tosyl-H's).)

c) 3-Triisopropylsilyloxy-19-nor-chol-1,3,5(10),16-tetraene-24-bromide [Formula (VII): $R^3$=α-$CH_3$, $R^4$=(i-Pr)$_3$Si, $R^5$=H, $Y^a$=($CH_2$)$_3$, L=Br, Δ16 double bond]

The 24-tosylate from (b) above (190 mg) in 1,2-dichloroethane (5 ml) and acetonitrile (5 ml) containing lithium bromide (300 mg) was heated under reflux for 3 hours. The reaction mixture was then cooled, diluted with ethyl acetate, washed with water then brine, and dried over sodium sulphate. Evaporation of the solvent gave the title compound (156 mg): NMR (CDCl$_3$) δ 0.9 (s, 18-H's), 3.5 (t, 24-H's), 5.2 (bs, 16-H), 6.5 and 6.95 (m, 1-, 2-, and 4-H's).

Preparation 2 a) 3-Triisopropylsilyloxy-19-nor-chol-1,3,5(10)-triene-24-carboxylic acid methyl ester [Formula (VII): $R^3$=α-$CH_3$, $R^4$=(i-Pr)$_3$Si, $R^5$=H, $Y^a$=$(CH_2)_2$, L=CO,O$CH_3$]

A solution of the Δ16, Δ22-pentaenic acid methyl ester used as starting material in Preparation 1(a) (200 mg) in ethyl acetate (10 ml) was treated with palladium/charcoal (400 mg, 10%) and stirred overnight under an atmosphere of hydrogen. Filtration through Celite and removal of the solvent under reduced pressure afforded the title compound (177 mg): NMR (CDCl$_3$) δ 0.96 (s, 18-H's), 3.7 (s, ester $CH_3$), 6.5 and 6.95 (m, 1-, 2- and 4-H's) (peaks at δ 5.2 and 5.6–5.9 were absent).

b) 3-Triisopropylsilyloxy-19-nor-chol-1,3,5(10)-trien-24-ol [Formula (VII): $R^3$=α-$CH_3$, $R^4$=(i-Pr)$_3$Si, $R^5$=H, $Y^a$=$(CH_2)_3$, L=OH]

The ester from (a) above (177 mg) was treated with lithium aluminium hydride (3 ml of a 1M solution in ether) for 3 hours at room temperature. The resulting product was worked up to give the title compound (158 mg): NMR (CDCl$_3$) δ 3.9 (t, 24-H's), 6.5 and 6.95 (m, 1-, 2- and 4-H's) (peak at δ 3.8 was absent).

c) 3-Triisopropylsilyloxy-19-nor-chol-1,3,5(10), triene-24-bromide [Formula (VII): $R^3$=α-$CH_3$, $R^4$=(i-Pr)$_3$Si, $R^5$=H, $Y^a$=$(CH_2)_3$, L=Br]

Treatment of the alcohol from (b) above (158 mg) with tosyl chloride as in Preparation 1(b), followed by treatment of the resulting toluene sulphonate (176 mg) with lithium bromide as in Preparation 1(c) afforded the title compound (131 mg): NMR (CDCl$_3$) δ 0.96 (s, 18-H's), 3.4 (t, 24-H's), 6.5 and 6.95 (m, 1-, 2- and 4-H's).

Preparation 3 a) 3-Triisopropylsilyloxy-20α-acetoxymethyl-19-nor-pregn-1,3,5(10),16-tetraene [Formula (VII): $R^3$=α-$CH_3$, $R^4$=(i-Pr)$_3$Si, $R^5$=H, $Y^a$=$CH_2$, L=O,CO, $CH_3$, Δ16 double bond]

A mixture of boron trifluoride etherate (50 μl) and acetic anhydride (0.6 ml) in dichloromethane (0.6 ml) was added dropwise to a solution of 3-triisopropylsilyloxy-19-nor-pregn-1,3,5(10),17(20)Z-tetraene (1.8 g) in dichloromethane (2 ml) containing acetic anhydride (0.9 ml) and paraformaldehyde (120 mg). The mixture was stirred for 2 hours, whereafter saturated sodium hydrogen carbonate was added and stirring was continued for 2 hours. The product was isolated by extraction into dichloromethane and purified by chromatography to give the title compound (1.5 g).

b) 3-Triisopropylsilyloxy-20α-hydroxymethyl-19-nor-pregn-1,3,5(10)-triene [Formula (VII): $R^3$=α-$CH_3$, $R^4$=(i-Pr)$_3$Si, $R^5$=H, $Y^a$=$CH_2$, L=OH, Δ16 double bond]

A solution of the product from (a) above (1.2 g) in ethanol (20 ml) containing 5% platinum on carbon (240 mg) was stirred under hydrogen for 2 days. Filtration and removal of the solvent afforded the 20-acetate of the title product (1.15 g), 480 mg of which was reduced with lithium aluminium hydride (1.2 ml of 1 M solution in ether) in ether (10 ml) to give the title compound (440 mg): IR (CDCl$_3$) υ$_{max}$ 1600, 3280 cm$^{-1}$; NMR (CDCl$_3$) δ 0.7 (s, 18-H's), 6.3–7.2 (m, 1-, 2- and 4-H's).

c) 3-Triisopropylsilyloxy-20α-tosyloxymethyl-19-nor-pregn-1,3,5(10)-triene [Formula (VII): $R^3$=α-$CH_3$, $R^4$=(i-Pr)$_3$Si, $R^5$=H, $Y^a$=$CH_2$, L=O,SO$_2$,$C_6H_4$, $CH_3$]

A solution of the alcohol from step (b) above (440 mg) in dichloromethane (2 ml) containing pyridine (0.5 ml) and tosyl chloride (445 mg) was stirred at room temperature overnight. The reaction mixture was then treated with aqueous sodium hydrogen carbonate and stirred for a further 2 hours, whereafter the product was extracted into dichloromethane and the extract was washed successively with water, 3% phosphoric acid and brine. Removal of the solvent followed by chromatography gave the title compound (485 mg): IR (CDCl$_3$) υ$_{max}$ 1600 cm$^{-1}$; NMR (CDCl$_3$) δ 0.66 (s, 18-H's), 2.33 (s, tosyl-Me), 3.5–4.2 (bm, 22-H's), 6.3–7.0 (m, 1-, 2- and 4-H's), 7.0, 7.9 (m, tosyl aryl-H's).

d) 3-Triisopropylsilyloxy-20α-bromomethyl-19-nor-pregn-1,3,5(10)-triene [Formula (VII): $R^3$=α-$CH_3$, $R^4$=(i-Pr)$_3$Si, $R^5$=H, $Y^a$=$CH_2$, L=Br]

The tosylate from step (c) above (485 mg) in a mixture of acetonitrile (16 ml) and dichloroethane (16 ml) containing lithium bromide (654 mg) was stirred overnight; water was then added and the product was extracted into dichloroethane. The extract was washed and dried, and the solvent was removed to give the title compound (360 mg). This product was used in further steps without further purification.

Preparation 4

3-Triisopropylsilyloxy-20α-formyl-19-nor-pregn-1, 3,5(10)-triene [Formula (IX): $R^3$=α-$CH_3$, $R^4$=(i-Pr)$_3$Si, $R^5$=H, $Y^b$=valence bond]

The 20-hydroxymethyl compound from Preparation 3(b) (220 mg) was stirred with pyridinium dichromate (1.25 mmol) in dichloromethane (3 ml) for 2 hours. Residual reagent was filtered off, the solvent was removed and the resulting material was purified by preparative thin layer chromatography (PTLC) to give the title compound (120 mg): IR (CDCl$_3$) υ$_{max}$ 1600, 1710 cm$^{-1}$; NMR (CDCl$_3$) δ 0.7 (s, 18-H's), 6.3–7.2 (m, 1-, 2- and 4-H's), 9.3,9.5 (d, CHO).

Preparation 5

2-Methoxy-3-triisopropylsilyloxy-19-nor-pregn-1,3, 5(10), 17(20)Z-tetraene

Sodium hydride (294 mg, 50%) in dimethylsulphoxide (6 ml) was stirred at 70° C. for 1 hour, then cooled to room temperature. Ethyltriphenylphosphonium iodide (2.75 g) in dimethylsulphoxide (10 ml) was added dropwise and the resulting mixture was stirred for 30 minutes. A solution of 2-methoxy-estrone-3-triisopropylsilyl ether (600 mg, prepared by silylation of the 3-OH compound with triisopropylsilyl chloride and imidazole in dichloromethane overnight at room temperature) in dimethylsulphoxide (10 ml) was added dropwise. The resulting solution was stirred for 30 minutes, whereafter the temperature was raised to 70° and stirring was continued overnight. The reaction mixture was cooled and worked up. Separation and purification of the products by chromatography gave the title compound (125 mg, see below) and the 3-OH analogue (300 mg): IR (CDCl$_3$) υ$_{max}$ 1590, 3520 cm$^{-1}$; NMR (CDCl$_3$) δ 0.9 (s, 18-H's), 1.67 (d, =CH—CH's), 3.8 (s, OCH's), 4.7–5.2 (q, =C$\underline{H}$Me), 6.5, 6.7 (s, 1,4-H's).

Silylation of this 3-OH compound (300 mg) as above and purification of the product by chromatography gave the title compound (370 mg): IR (CDCl$_3$) $\upsilon_{max}$ 1600 cm$^{-1}$; NMR (CDCl$_3$) δ 0.9 (s, 18-H's), 1.68 (d, =CH—CH's), 3.7 (s, OCH's), 4.7–5.3 (q, =CH—Me), 6.4, 6.6 (s, 1,4-H's).

Preparation 6 a) 2-Methoxy-3-triisopropylsilyloxy-19-nor-chol-1, 3,5(10),16-tetraene-24-carboxylic acid methyl ester [Formula (VI): R$^3$=α-CH$_3$, R$^4$=(i-Pr)$_3$Si, R$^5$=OCH$_3$, R9=CH3, Y=(CH$_2$)$_2$, Δ16 double bond]

Ethyl aluminium dichloride (1.4 ml, 2.4 mmol, in toluene) was added dropwise to a solution of the product from Preparation 5 (370 mg) in dichloromethane (4 ml) containing methyl acrylate (144 μl). The resulting mixture was stirred for 4 hours, whereafter further methyl acrylate (144 μl) was added and stirring was continued overnight. The reaction mixture was then worked up and the product was purified by chromatography to give the title compound (345 mg): IR (CDCl$_3$) $\upsilon_{max}$ 1600, 1720 cm$^{-1}$; NMR (CDCl$_3$) δ 0.8 (s, 18-H's), 3.6 (s, OCH's), 5.1–5.4 (bs, 16-H's), 6.4, 6.58 (s, 1,4-H's).

b) 2-Methoxy-3-triisopropylsilyloxy-19-nor-chol-1, 3,5(10),16-tetraen-24-ol [Formula (VII): R$^3$=α-CH$_3$, R$^4$=(i-Pr)$_3$Si, R$^5$=OCH$_3$, L=OH, Y$^a$=(CH$_2$)$_3$, Δ16 double bond]

Lithium aluminium hydride (1 ml of a 1 M solution in ether) was added dropwise to a solution of the ester from (a) above (265 mg) in ether (5 ml), whereafter the reaction mixture was stirred for 30 minutes, diluted with ether and quenched with wet sodium sulphate, giving crude title compound (248 mg): IR (CDCl$_3$) $\upsilon_{max}$ 1600, 3380–3660 cm$^{-1}$; NMR (CDCl$_3$) δ 0.8 (s, 18-H's), 3.3–3.8 (b, HOCH's), 3.7 (s, OCH's), 5.1–5.4 (bs, 16-H's), 6.4, 6.6 (s, 1,4-H's).

c) 2-Methoxy-3-triisopropylsilyloxy-19-nor-chol-1, 3,5(10),16-tetraen-24-ol, 24-tosylate [Formula (VII): R$^3$=α-CH$_3$, R$^4$=(i-Pr)$_3$Si, R$^5$=OCH$_3$, L=O, SO$_2$,C$_6$H$_4$,CH$_3$, Y$^a$=(CH$_2$)$_3$, Δ16 double bond]

A solution of the alcohol from (b) above (248 mg) in dichloromethane (4 ml) containing tosyl chloride (290 mg) and pyridine (250 μl) was stirred overnight. Work up and purification by chromatography gave the title compound (245 mg): IR (CDCl$_3$) $\upsilon_{max}$ 1595 cm$^{-1}$; NMR (CDCl$_3$) δ 0.7 (s, 18-H's), 2.4 (s, tosyl-Me), 3.8–4.1 (b, TsOCH's), 3.7 (s, OCH's), 5.0–5.3 (bs, 16-H's), 6.4, 6.56 (s, 1,4-H's), 7.0–7.8 (ABq, tosyl arH's).

d) 2-Methoxy-3-triisopropylsilyloxy-19-nor-chol-1, 3,5(10),16-tetraene-24-bromide [Formula (VII): R$^3$=α-CH$_3$, R$^4$=(i-Pr)$_3$Si, R$^5$=OCH$_3$, L=Br, Y$^a$=(CH$_2$)$_3$, Δ16 double bond]

The tosylate from (c) above (245 mg) was dissolved in dichloroethane (6 ml) and acetonitrile (6 ml) containing lithium bromide (310 mg) and the resulting mixture was heated under reflux for 3 hours. The mixture was worked up and the product was purified by chromatography to give the title compound (200 mg): IR (CDCl$_3$) υmax 1600 cm$^{-1}$; NMR (CDCl$_3$) δ 0.83 (s, 18-H's), 3.2–3.5 (b, BrCH's), 3.73 (s, OCH's), 5.1–5.4 (bs, 16-H's), 6.43, 6.56 (s, 1,4-H's).

e) 2-Methoxy-3-triisopropylsilyloxy-20α-formyl-19-nor-pregn-1,3,5(10)-triene [Formula (IX): R$^3$=α-CH$_3$, R$^4$=(i-Pr)$_3$Si, R$^5$=OCH$_3$, Y$^b$=valence bond]

This is prepared from the product of Preparation 5 according to the procedures of Preparations 3(a), 3(b) and 4.

f) 2-Methoxy-3-triisopropylsilyloxy-20α-bromomethyl-19-nor-pregn-1,3,5(10)-triene [Formula (VII): R$^3$=α-CH$_3$, R$^4$=(i-Pr)$_3$Si, R$^5$=OCH$_3$, Y$^a$=CH$_2$, L=Br]

This is prepared from the product of Preparation 5 according to the procedures of Preparations 3(a)–(d).

Preparation 7 a) 3-Triisopropylsilyloxy-19-nor-pregn-1,3,5(10), 6, 8,17(20)Z-hexaene

3-Hydroxy-19-nor-androst-1,3,5(10),6,8 pentaen-17-one was subjected to a Wittig reaction followed by silylation as in Preparation 5 to give the title compound: IR (CDCl$_3$) $\upsilon_{max}$ 1590, 1610 cm$^{-1}$; NMR (CDCl$_3$) δ 0.73 (s, 18-H's), 1.73 (d, =CH—CH's), 4.8–5.5 (q, =CH—Me), 6.7, 8.0 (s, 1-, 2-, 4-,6- and 7-H's).

b) 3-Triisopropylsilyloxy-19-nor-chol-1,3,5 (10), 6, 8,16-hexaene-24-carboxylic acid methyl ester [Formula (VI): R$^3$=α-CH$_3$, R$^4$=(i-Pr)$_3$Si, R$^5$=H, R9=CH3, Y=(CH$_2$)$_2$, Δ6, Δ8 and Δ16 double bonds]

The product from (a) above was subjected to an ene reaction as in Preparation 6(a) to give the title compound: IR (CDCl$_3$) $\upsilon_{max}$ 1590, 1610, 1725 cm$^{-1}$; NMR (CDCl$_3$) δ 0.67 (s, 18-H's), 0.82 (d, 21-H's), 2.9–3.5 (bm, 23-H's), 3.63 (s, COOCH's), 5.2–5.6 (bs, 16-H's), 6.7, 8.0 (s, 1-, 2-, 4-, 6- and 7-H's).

c) 3-Triisopropylsilyloxy-19-nor-chol-1,3,5(10), 6,8, 16-hexaen-24-ol [Formula (VII): R$^3$=α-CH$_3$, R$^4$=(i-Pr)$_3$Si, R$^5$=H, L=OH, Y$^a$=(CH$_2$)$_3$, Δ6, Δ8 and Δ16 double bonds]

The product from (b) above was reacted as in Preparation 6(b) to give the title compound: IR (CDCl$_3$) $\upsilon_{max}$ 1590, 1600, 3360–3660 cm$^{-1}$; NMR (CDCl$_3$) δ 0.66 (s, 18-H's), 0.82 (d, 21-H's), 3.4–3.9 (b, HOCH's), 5.2–5.5 (bs, 16-H's), 6.8–8.0 (s, 1-, 2-, 4-, 6- and 7-H's)

d) 3-Triisopropylsilyloxy-19-nor-chol-1,3,5(10), 6,8, 16-tetraen-24-ol, 24-tosylate [Formula (VII): R$^3$=α-CH$_3$, R$^4$=(i-Pr)$_3$Si, R$^5$=H, L=O,SO$_2$,C$_6$H$_4$,CH$_3$, Y$^a$=(CH$_2$)$_3$, Δ6, Δ8 and Δ16 double bonds]

The product from (c) above was reacted as in Preparation 6(c) to give the title compound: IR (CDCl$_3$) $\upsilon_{max}$ 1590, 1610 cm$^{-1}$; NMR (CDCl$_3$) δ 0.6 (s, 18-H's), 0.78 (d, 21-H's), 2.4 (s, tosyl-Me), 3.8–4.3 (b, TsOCH's), 5.2–5.5 (bs, 16-H's), 6.8–8.1 (m, 1-, 2-, 4- and tosyl arH's).

e) 3-Triisopropylsilyloxy-19-nor-chol-1,3,5(10),6,8, 16-hexaene-24-bromide [Formula (VII): R$^3$=α-CH$_3$, R$^4$=(i-Pr)$_3$, Si, R$^5$=OCH$_3$, L=Br, Y$^a$=(CH$_2$)$_3$, Δ6, Δ8 and Δ16 double bonds]

This was prepared by reacting the tosylate from (d) above according to the method of Preparation 6(d) to give the title compound: IR (CDCl$_3$) $\upsilon_{max}$ 1590, 1600 cm$^{-1}$; NMR (CDCl$_3$) δ 0.66 (s, 18-H's), 5.2–5.5 (bs, 16-H's), 6.8–8.0 (m, 1-, 2-, 4-, 6- and 7-H's)

Preparation 8 a) 3-Tetrahydropyranyloxy-19-nor-pregn-1,3,5 (10), 17(20)E-tetraene-21-carboxylic acid ethyl ester A solution of estrone-3-tetrahydropyranyl ether (1.25 g, prepared according to J. Chem. Soc. Perkin, pp. 1282–1286,

[1978]) in ethanol (18 ml) containing diethyl ethoxycarbonylmethylphosphonate (2.65 ml) was treated with sodium ethoxide (6.75 ml of a 21% solution in ethanol) and heated under reflux for 15 hours. After work up the product was purified by chromatography to afford the title compound (1.12 g): IR (CDCl$_3$) $\upsilon_{max}$ 1450–1600, 1645, 1695 cm$^{-1}$; NMR (CDCl$_3$) δ 0.8 (s, 18-H's), 3.55 (m, six H's of THP), 4.05 (q, COOCH's), 5.25 (m, two H's of THP), 5.45 (20-H), 6.7–7.05 (m, 1-, 2- and 4-H's).

b) 3-Tetrahydropyranyloxy-19-nor-pregn-1,3,5(10), 17(20)E-tetraen-21-ol

Lithium aluminium hydride (4.9 ml of a 1 M solution in ether) was added to a solution of the ester from (a) above (1 g) in ether (4 ml). After 4 hours the reaction was quenched with wet sodium sulphate, the reaction mixture was worked up and the solvent was removed to give the title compound (0.9 g): IR (CDCl$_3$) $\upsilon_{max}$ 1610, 3580 cm$^{-1}$; NMR (CDCl$_3$) δ 0.76 (s, 18-H's), 3.35 (m, six H's of THP), 3.95 (d, 21-H's), 5.25 (m, two H's of THP), 5.1 (20-H), 6.7–7.05 (m, 1-, 2- and 4-H's).

c) 3-Triisopropylsilyloxy-19-nor-pregn-1,3,5(10), 17(20)E-tetraene

A solution of the alcohol from (b) above (0.9 g) in tetrahydrofuran (10 ml) at 0° was treated with pyridinium sulphate (576 mg). The resulting mixture was stirred for 4 hours, whereafter lithium aluminium hydride (9.6 ml of a 1M solution in tetrahydrofuran) was added and stirring was continued for 1 hour at 0° and then at room temperature overnight. The crude product (0.7 g), containing a mixture of the 3-OH compound and the 3-THP ether, was cleaved by storage overnight in acetone (15 ml) containing p-toluenesulphonic acid (150 mg of hydrate). The cleaved 3-OH product (700 mg) was silylated by treatment with chlorotriisopropylsilane (623 μl) in dichloromethane (3 ml) containing imidazole (720 mg) at room temperature overnight, and following work up gave the title compound (800 mg): IR (CDCl$_3$) $\upsilon_{max}$ 1610, 1600–1450 (three bands) cm$^{-1}$; NMR (CDCl$_3$) δ 0.78 (s, 18-H's), 1.05–1.2 (silyl H's), 1.50 (d, 21-H's), 5.0 (q, 20-H), 6.5–6.95 (m, 1-, 2- and 4-H's).

d) 3-Triisopropylsilyloxy-20-epi-19-nor-chol-1,3,5(10),16,22-pentane-24-carboxylic acid methyl eater [Formula (VI): R$^3$=β-CH$_3$, R$^4$=(i-Pr)$_3$Si, R$^5$=H, RO=CH3, Y=CH=CH, Δ16 double bond]

A solution of the E-alkene from (c) above (800 mg) in benzene was treated with diethyl aluminium chloride (3.19 ml) and methyl propiolate (0.415 ml) and stirred for 3 days. The reaction mixture was then worked up and the product was purified by chromatography to give the title compound: IR (CDCl$_3$) $\upsilon_{max}$ 1640, 1710 cm$^{-1}$; NMR (CDCl$_3$) δ 0.78 (s, 18-H's), 3.5 (s, OCH's), 4.0 (by product), 5.2 (t, 16-H's), 6.5, 6.95 (s, 1-, 2- and 4-H's).

e) 3-Triisopropylsilyloxy-20-epi-19-nor-chol-1,3,5(10),16-tetraen-24-ol [Formula (VII): R$^3$=β-CH$_3$, R$^4$=(i-Pr)$_3$Si, R$^5$=H, L=OH, Y$^a$=(CH$_2$)$_3$, Δ16 double bond]

Treatment of the ester from (d) above (400 mg) with lithium aluminium hydride according to the method of Preparation 6(b) (except with inverse addition) and work up gave the title compound (360 mg, mixed with the 22,23 unsaturated alcohol in a ratio of approximately 85:15): IR (CDCl$_3$) $\upsilon_{max}$ 1600, 3580 cm$^{-1}$; NMR (CDCl$_3$) δ 0.78 (s, 18-CH's), 3.5 (m, HOCH's), 3.7 (s, OCH's), 5.1–5.4 (bs, 16-H's), 6.4, 6.6 (s, 1-, 2- and 4-H's).

f) 3-Triisopropylsilyloxy-20-epi-19-nor-chol-1,3,5(10),16-tetraen-24-ol, 24-tosylate [Formula (VII): R$^3$=β-CH$_3$, R$^4$=(i-Pr)$_3$Si, R$^5$=H, L=O,SO$_2$,C$_6$H$_4$, CH$_3$, Y$^a$=(CH$_2$)$_3$, Δ16 double bond]

The alcohol from (e) above (360 mg) was tosylated as in Preparation 6(c). The desired product was separated from the "unreacted" 22,23 unsaturated alcohol by chromatography to give the title compound (380 mg): NMR (CDCl$_3$) δ 0.78 (s, 18-H's), 2.4 (s, tosyl-Me), 3.95 (t, TsOCH's), 5.15 (bs, 16-H's), 6.4, 6.95 (s, 1,4-H's), 7.2–7.7 (ABq, tosyl arH's).

g) 3-Triisopropylsilyloxy-20-epi-19-nor-chol-1,3,5(10),16-tetraene-24-bromide [Formula (VII): R$^3$=β-CH$_3$, R$^4$=(i-Pr)$_3$Si, R$^5$=H, L=Br, Y$^a$=(CH$_2$)$_3$, Δ16 double bond]

The tosylate from (f) above (500 mg) was dissolved in a mixture of dichloroethane (13 ml) and acetonitrile (13 ml) containing lithium bromide (700 mg) and the resulting mixture was heated under reflux for 3.5 hours. The mixture was then worked up and the product was purified by chromatography to give the title compound (350 mg): NMR (CDCl$_3$) δ 0.78 (s, 18-H's), 3.35 (b, BrCH's), 5.25 (bs, 16-H's), 6.5, 6.95 (s, 1,4-H's).

h) 3-Triisopropylsilyloxy-20β-formyl-19-nor-pregn-1,3,5(10)-triene [Formula (IX): R$^3$=β-CH$_3$, R$^4$=(i-Pr)$_3$Si, R$^5$=H, Y$^b$=valence bond]

This is prepared from the product of Preparation 8(c) according to the procedures of Preparations 3 (a), 3 (b) and 4.

i) 3-Triisopropylsilyloxy-20β-bromomethyl-19-nor-pregna-1,3,5(10)-triene [Formula (VII): R$^3$=β-CH$_3$, R$^4$=(i-Pr)$_3$Si, R$^5$=H, Y$^a$=CH$_2$, L=BR]

This is prepared from the product of Preparation 8(c) according to the procedures of Preparations 3(a)–(d)

Preparation 9 a) 3-Triisopropylsilyloxy-19-nor-pregn-1,3,5(10), 8, 17(20)Z-pentane

3-Hydroxy-19-nor-androst-1,3,5(10),8-tetraen-17-one was subjected to a Wittig reaction followed by silyation as in Preparation 5 to give the title compound: IR (CDCl$_3$) $\upsilon_{max}$ 1600 cm$^{-1}$; NMR (CDCl$_3$) δ 0.8 (s, 18-H's), 4.8–5.4 (b, =CH—Me, 8H), 6.7–7.3 (m, 1-, 2- and 4-H's).

b) 3-Triisopropylsilyloxy-19-nor-chol-1,3,5(10), 6.16-pentaene-24-carboxylic acid methyl ester [Formula (VI): R$^3$=α-CH$_3$, R$^4$=(i-Pr)$_3$Si, R$^5$=H, R$^9$=CH$_3$, Y=(CH$_2$)$_2$, Δ6 and Δ16 double bonds]

The product from (a) above was subjected to an ene reaction as in Preparation 6(a) to give the title compound: IR (CDCl$_3$) $\upsilon_{max}$ 1590, 1610, 1725 cm$^{-1}$; NMR (CDCl$_3$) δ 0.67 (s, 18-CH's), 3.8–4.3 (q, COOCH's), 5.2–5.6 (bs, 16-H's), 6.8–8.0 (s, 1-, 2-, 4- and 6-H's).

c) 3-Triisopropylsilyloxy-19-nor-chol-1,3,5(10), 6, 16-pentaen-24-ol [Formula (VII): R$^3$=α-CH$_3$, R$^4$=(i-Pr)$_3$Si, R$^5$=H, L=OH, Y$^a$=(CH$_2$)$_3$, Δ16 and Δ16 double bonds]

Reaction of the product from (b) above as in Preparation 6(b) gave the title compound: IR (CDCl$_3$) $\upsilon_{max}$ 1595, 1620, 3300–3640 cm$^{-1}$; NMR (CDCl$_3$) δ 0.7 (s, 18-CH's), 3.3–3.8 (b, HOCH's), 5.1–5.5 (b, 16-H's), 6.8–7.9 (s, 1-, 2-, 4- and 6-H's).

d) 3-Triisopropylsilyloxy-19-nor-chol-1,3,5(10),6,16-pentaen-24-ol, 24-tosylate [Formula (VII): R$^3$=α-CH$_3$, R$^4$=(i-Pr)$_3$Si, R$^5$=H, L=O,SO$_2$,C$_6$H$_4$,CH$_3$, Y$^a$=(CH$_2$)$_3$, Δ6 and Δ16 double bonds]

Reaction of the product from (c) above as in Preparation 6(c) gave the title compound: IR (CDCl$_3$) υ$_{max}$ 1590,1625 cm$^{-1}$; NMR (CDCl$_3$) δ 0.6 (s, 18-CH's), 2.37 (s, tosyl-Me), 3.7–4.2 (b, TsOCH's), 5.1–5.5 (b, 16-H's), 6.7–7.9 (m, 1-, 2-, 4-, 6- and tosyl arH's).

e) 3-Triisopropylsilyloxy-19-nor-chol-1,3,5(10),6,16-pentaene-24-bromide [Formula (V): R$^3$=α-CH$_3$, R$^4$=(i-Pr)$_3$Si, R$^5$=H, L=Br, Y$^a$=(CH$_2$)$_3$, Δ6 and Δ16 double bonds]

Reaction of the tosylate from (d) above according to the method of Preparation 6(d) gave the title compound: IR (CDCl$_3$) υ$_{max}$ 1585, 1610 cm$^{-1}$; NMR (CDCl$_3$) δ 0.63 (s, 18-H's), 5.1–5.5 (b, 16-H's), 6.7–7.9 (m, 1-, 2-, 4- and 6-H's).

EXAMPLE 1 a) 3-Triisopropylsilyloxy-23,23a-bishomo-19-nor-chol-1,3,5(10)16-tetraene-24-nitrile [Formula (II): R$^3$=α-CH$_3$, R$^4$=(i-Pr)$_3$Si, R$^5$=H, Y=(CH$_2$)$_4$, Δ16 double bond]

A solution of acetonitrile (0.16 ml) in tetrahydrofuran (1.5 ml) was added dropwise at −78° to a solution of butyl lithium in hexane (3 mM in 1.9 ml) and the reaction mixture was stirred for 50 minutes. The bromide from Preparation 1(c) (150 mg) in tetrahydrofuran (3 ml+1 ml wash) was added and the mixture was stirred for a further hour then warmed to −30° for an hour. TLC indicated the absence of starting material, so the mixture was cooled to −78° and treated with ammonium chloride. The product was extracted into ether and worked up to afford the title compound (85 mg): IR υ$_{max}$ 2250, 1620 cm$^{-1}$; NMR (CDCl$_3$) δ 0.96 (s, 18-H's), 5.2 (bs, 16-H), 6.5 and 6.95 (m, 1-, 2- and 4-H's).

b) 25-Amino-3-triisopropylsilyloxy-24-homo-19-nor-cholest-1,3,5(10),16-tetraene [Formula (I): R$^1$=R$^2$=CH$_3$, R$^3$α-CH$_3$, R$^4$=(i-Pr)$_3$Si, R$^5$=H, X=NH$_2$, Y=(CH$_2$)$_4$, Δ16 double bond]

Anhydrous cerous chloride was prepared by heating CeCl$_3$.7H$_2$O (2 g) in vacuo (<0.1 mm Hg) first at 70° for 1 hour, then at 110° for 1 hour and finally at 145° for 2½ hours. Thus-obtained anhydrous cerous chloride (256 mg) was heated in vacuo at 130° for 2 hours, cooled, then suspended in tetrahydrofuran (3 ml); the resulting mixture was kept overnight with stirring. The suspension was cooled to −78° and then treated with methyl lithium (0.86 ml of a 1.4 M solution in ether). The mixture was stirred for 15 minutes at −78°, 15 minutes at 0°, then cooled to −78° and the nitrile from (a) above (84 mg) in tetrahydrofuran (2 ml+1 ml wash) was added dropwise. After a further hour at −78° (TLC control), ammonium hydroxide was added and the mixture was warmed to room temperature and filtered through Celite (methylene chloride wash). Removal of the solvents gave the title compound (67 mg, isolated by chromatography): IR υ$_{max}$ 1620 cm$^{-1}$; NMR (CDCl$_3$) δ 0.96 (s, 18-H's), 0.99 (21-H's), 1.25 (25-H's), 5.2 (bs, 16-H), 6.5 and 6.95 (m, 1-, 2- and 4-H's).

c) 25-Acetylamino-3-triisopropylsilyloxy-24-homo-19-nor-cholest-1,3,5(10),16-tetraene [Formula (I): R$^1$=R$^2$=CH$_3$, R$^3$=α-CH$_3$, R$^4$=(i-Pr)$_3$Si, R$^5$=H, X=NH(COCH$_3$), Y=—(CH$_2$)$_4$, Δ16 double bond]

The amine from (b) above (67 mg) in dichloromethane (2 ml) containing pyridine (0.475 ml) and acetic anhydride (0.475 ml) was stirred for 4 hours, whereafter the mixture was diluted with dichloromethane, treated with aqueous sodium bicarbonate, and stirred overnight. Work up afforded the title compound (70 mg, isolated by preparative TLC): IR υ$_{max}$ 1690, 1620, 1600–1450 cm$^{-1}$; NMR (CDCl$_3$) δ 0.96 (s, 18-H's), 0.99 (21-H's), 1.25 (25-H's), 1.9 (s, COCH's) 5.0 (s, NH), 5.15 (bs, 16-H), 6.5 and 6.95 (m, 1-, 2- and 4-H's).

d) 25-Acetylamino-3-hydroxy-24-homo-19-nor-cholest-1,3,5(10),16-tetraene [Formula (I): R$^1$=R$^2$=CH$_3$, R$^3$=α-CH$_3$, R$^4$=R$^5$=H, X=NH(COCH$_3$), Y=(CH$_2$)$_4$, Δ16 double bond]

The silyl compound from (c) above (70 mg) in tetrahydrofuran (1.5 ml) was desilylated by treatment overnight with tetrabutylammonium fluoride (1.3 ml of a 1 M solution in tetrahydrofuran). The crude product (40 mg) was purified by TLC to give the title compound (27 mg): NMR (CDCl$_3$) δ 0.76 (s, 18-H's), 0.95, 1.0 (21-H's), 1.3 (25-H's), 1.9 (s, COCH's), 5.1–5.3 (m, NH, 16-H), 6.5 and 6.95 (m, 1-, 2- and 4-H's).

e) 25-Ethylamino-3-hydroxy-24-homo-19-nor-cholest-1,3,5(10),16-tetraene [Formula (I): R$^1$=R$^2$=CH$_3$, R$^3$=α-CH$_3$, R$^4$=(i-Pr)$_3$Si, R$^5$=H, X=NH(CH$_2$CH$_3$), Y=(CH$_2$)$_4$, Δ16 double bond]

The title compound is prepared by reduction of the product of (c) above with lithium aluminium hydride in tetrahydrofuran for 3 hours followed by removal of the silyl group according to step (d) above.

f) 25-Methylamino-3-hydroxy-24-homo-19-nor-cholest-1,3,5(10),16-tetraene [Formula (I): R$^1$=R$^2$=CH$_3$, R$^3$=α-CH$_3$, R$^4$=(i-Pr)$_3$Si, R$^5$=H, X=NH(CH$_3$), Y=(CH$_2$)$_4$, Δ16 double bond]and 25-dimethylamino-3-hydroxy-24-homo-19-nor-cholest-1,3,5(10),16-tetraene [Formula (I): R$^1$=R$^2$=CH$_3$, R$^3$=α-CH$_3$, R$^4$=(i-Pr)$_3$Si, R$^5$=H, X=N(CH$_3$)$_2$, Y=(CH$_2$)$_4$, Δ16 double bond]

The title compounds are prepared by methylation with methyl iodide/calcium oxide of the product from (c) above and separation of the products by chromatography followed by desilylation as in step (d) above.

g) 25-(N-Ethyl-N-methylamino)-3-hydroxy-24-homo-19-nor-cholest-1,3,5(10),16-tetraene [Formula (I): R$^1$=R$^2$=CH$_3$, R$^3$=α-CH$_3$, R$^4$=(i-Pr)$_3$Si, R$^5$=H, X=N(CH$_3$)(CH$_2$CH$_3$), Y=(CH$_2$)$_4$, Δ16 double bond]

The title compound is prepared by methylation of the N-ethyl 3-silyl ether compound prepared as an intermediate in step (e) above, followed by desilylation according to the procedure in step (d) above.

h) 25-Acetylamino-3-methoxy-24-homo-19-nor-cholest-1,3,5(10),16-tetraene [Formula (I): R$^1$=R$^2$=CH$_3$, R$^3$=α-CH$_3$, R$^4$=CH$_3$, R$^5$=H, X=NH(COCH$_3$), Y=(CH$_2$)$_4$, Δ16 double bond]

The title compound is prepared by methylation of the product of Example 1(d) with sodium hydride/methyl iodide.

i) 25-Acetylamino-3-ethoxy-24-homo-19-nor-cholest-1,3,5(10), 16-tetraen [Formula (I): $R^1=R^2=CH_3$, $R^3=\alpha\text{-}CH_3$, $R^4=CH_3CH_2$, $R^5=H$, $X=NH(COCH_3)$, $Y=(CH_2)_4$, $\Delta 16$ double bond]

The title compound is prepared as in step (h) above using ethyl iodide in place of methyl iodide.

j) 25-Acetylamino-3-ethoxy-24-homo-19-nor-cholest-1,3,5(10), 16-tetraen [Formula (I): $R^1=R^2=CH_3$, $R^3=\alpha\text{-}CH_3$, $R^4=(CH_3)_2CHCH_2$, $R^5=H$, $X=NH(COCH_3)$, $Y=(CH_2)_4$, $\Delta 16$ double bond]

The title compound is prepared as in step (h) above using isobutyl bromide in place of methyl iodide.

Alternatively, analogues of any of the compounds in the Examples having $R^4$=lower alkyl may be prepared by starting from the corresponding estrone 3-ether and following the remaining steps without modification.

k) 25-Benzamido-3-hydroxy-24-homo-19-nor-cholest-1,3,5(10),16-tetraene [Formula (I): $R^1=R^2=CH_3$, $R^3=\alpha\text{-}CH_3$, $R^4=R^5=H$, $X=NH(COC_3H_5)$, $Y=(CH_2)_4$, $\Delta 16$ double bond]

The title compound is prepared by substituting benzoyl chloride for acetic anhydride in step (c) above and desilylating the resulting product as in step (d) above.

l) 25-Phenylacetylamino-3-hydroxy-24-homo-19-nor-cholest-1,3,5(10),16-tetraene [Formula (I): $R^1=R^2=CH_3$, $R^3=\alpha\text{-}CH_3$, $R^4=R^5=H$, $X=NH(CO,CH_2,C_6H_5)$, $Y=(CH_2)_4$, $\Delta 16$ double bond]

The title compound is prepared by substituting phenylacetyl chloride for acetic anhydride in step (c) above and desilylating the resulting product as in step (d) above.

EXAMPLE 2 a) 3-Triisopropylsilyloxy-23,23a-bishomo-19-nor-chol-1,3,5(10)-tetraene-24-nitrile [Formula (II): $R^3=\alpha\text{-}CH_3$, $R^4=(i\text{-}Pr)_3Si$, $R^5=H$, $Y=(CH_2)_4$]

The bromide from Preparation 2(c) (130 mg) was treated with α-lithio-acetonitrile as in Example 1 (a) to give the title compound (140 mg crude, 65 mg after chromatography): IR $\upsilon_{max}$ 2250 cm$^{-1}$; NMR (CDCl$_3$) δ 0.80 (s, 18-H's), 6.5 and 6.95 (m, 1-, 2- and 4-H's).

b) 25-Amino-3-triisopropylsilyloxy-24-homo-19-nor-cholest-1,3,5(10)-tetraene [Formula (I): $R^1=R^2=CH_3$, $R^3=\alpha\text{-}CH_3$, $R^4=(i\text{-}Pr)_3Si$, $X=NH_2$, $Y=(CH_2)_4$]

The nitrile from (a) above (65 mg) was treated with methyl cerous chloride as in Example 1 (b) to give the title compound (58 mg): NMR (CDCl$_3$) δ 0.80 (s, 18-H's), 1.3 (s, 25-H's), 6.5 and 6.95 (m, 1-, 2- and 4-H's).

c) 25-Acetylamino-3-triisopropylsilyloxy-24-homo-19-nor-cholest-1,3,5(10)-triene [Formula (I): $R^1=R^2=CH_3$, $R^3=\alpha\text{-}CH_3$, $R^4=(i\text{-}Pr)_3Si$, $R^5=H$, $X=NH(COCH_3)$, $Y=(CH_2)_4$]

The amine from (b) above (58 mg) was acetylated as in Example 1(c) to give the title compound (57 mg): NMR (CDCl$_3$) δ 0.80 (s, 18-H's), 1.3 (s, 25-H's), 1.9 (s, COCH's), 5.1 (s, NH), 6.5 and 6.95 (m, 1-, 2- and 4-H's).

d) 25-Acetylamino-3-hydroxy-24-homo-19-nor-cholest-1,3,5(10)-triene [Formula (I): $R^1=R^2=CH_3$, $R^3=\alpha\text{-}CH_3$, $R^4=H$, $R^5=H$, $X=NH(COCH_3)$, $Y=(CH_2)_4$]

The silyl ether from (c) above (57 mg) was desilylated as in Example 1 (d) to give the title compound (51 mg crude, 15 mg purified by TLC): NMR (CDCl$_3$) δ 0.80 (s, 18-H's), 1.3 (s, 25-H's), 1.9 (s, COCH's), 5.0–5.15 (s, NH), 6.5 and 6.95 (m, 1-, 2- and 4-H's).

EXAMPLE 3 a) 3-Triisopropylsilyloxy-19,26,27-trisnor-cholest-1,3,5(10)-trien-24-one [Formula (V): $R^1=CH_3$, $R^3=\alpha\text{-}CH_3$, $R^4=(i\text{-}Pr)_3Si$, $R^5=H$, $Y=(CH_2)_2$]

Butyl lithium (0.94 ml, 1.5 mM) was added dropwise to 1-triphenylphosphoranylidene-2-propanone (477 mg) in tetrahydrofuran (12 ml) at −78° and the mixture was stirred for 30 minutes. The bromide from Preparation 3(d) above (260 mg) in tetrahydrofuran (3 ml) was added dropwise at −78° and the reaction mixture was stirred for 30 minutes, allowed to warm to 0° and then stirred for a further 3 hours. After storage overnight at room temperature the solvent was removed and the residue was dissolved in ethanol (15 ml) and water (6 ml) and heated under reflux overnight. The crude product, which had undergone in situ desilylation, was purified by chromatography to give the 3-OH analogue of the title compound (160 mg): IR (CDCl$_3$) $\upsilon_{max}$ 1600, 1700, 3160–3460 cm$^{-1}$; NMR (CDCl$_3$) δ 0.67 (s, 18-H's), 2.13 (s, 25-H's), 6.3–7.3 (m, 1-, 2- and 4-H's).

This product was silylated by treatment with triisopropylsilyl chloride (130 mg) and imadazole (122 mg) in dichloromethane (1 ml) and purified by chromatography to give the title compound: IR (CDCl$_3$) $\upsilon_{max}$ 1600, 1700 cm$^{-1}$; NMR (CDCl$_3$) δ 0.67 (s, 18-H's), 2.07 (s, 25-H's), 6.3–7.2 (m, 1-, 2- and 4-H's).

b) 3-Triisopropylsilyloxy-24-propargyl-19,26,27-trisnor-cholest-1,3,5(10)-trien-24-ol [Formula (I): $R^1=CH_3$, $R^2=CH_2C\equiv CH$, $R^3=\alpha\text{-}CH_3$, $R^4=(i\text{-}Pr)_3Si$, $R^5=H$, $X=OH$, $Y=(CH_2)_2$]

A reagent solution was prepared as follows: propargyl bromide (2.53 g, 80% by weight in toluene) in ether (18 ml) was added dropwise to aluminium powder (900 mg) and powdered mercuric chloride (45 mg) in ether (4 ml) and the mixture was refluxed overnight. The total volume of the resulting solution was 24 ml. A portion of this reagent (0.8 ml) was added dropwise to a solution of the ketone from (a) above (60 mg) in tetrahydrofuran (1 ml), and the resulting mixture was stirred at room temperature for 15 minutes. Ether and wet sodium sulphate were then added to coagulate the aluminium compounds, whereafter the solution was filtered and the solvents were removed to give the title compound (55 mg): IR (CDCl$_3$) $\upsilon_{max}$ 1600, 3280 cm$^{-1}$; NMR (CDCl$_3$) δ 0.7 (s, 18-H's), 6.3–7.2 (m, 1-, 2- and 4-H's).

c) 3,24-Dihydroxy-24-propargyl-19–26,27-trisnor-cholest-1,3,5(10)-triene [Formula (I): $R^1=CH_3$, $R^2=CH_2C\equiv CH$, $R^3=\alpha\text{-}CH_3$, $R^4=R^5=H$, $X=OH$, $Y=(CH_2)_2$]

The product from (b) above (55 mg) was desilylated as in Example 1(d) to give the title compound (38 mg): IR (CDCl$_3$) $\upsilon_{max}$ 1590, 1600, 3300, 3310–3620 cm$^{-1}$; NMR (CDCl$_3$) δ 0.7 (s, 18-H's), 1.2 (9, C≡CH), 4.6–5.1 (bs, OH), 6.3–7.2 (m, 1-, 2- and 4-H's).

d) 2-Methoxy-3,24-dihydroxy-24-propargyl-19,26,27-trisnor-cholesta-1,3,5(10)-triene [Formula (I): $R^1=CH_3$, $R^2=CH_2C\equiv CH$, $R^3=\alpha\text{-}CH_3$, $R^4=H$, $R^5=OCH_3$, $X=OH$, $Y=(CH_2)_2$]

This is prepared from the bromide of Preparation 6(d) by the procedures of steps (a)–(d) above.

e) 3,24-Dihydroxy-20-epi-24-propargyl-19,26,27-trisnor-cholest-1,3,5(10)-triene [Formula (I): $R^1$=$CH_3$, $R^2$=$CH_2C\equiv CH$, $R^3$=β-$CH_3$, $R^4$=$R^5$=H, X=OH, Y=$(CH_2)_2$]

This is prepared from the bromide of Preparation 8(i) by the procedures of steps (a)–(d) above.

EXAMPLE 4 a) 3-Triisopropylsilyloxy-19-nor-chol-1,3,5(10), 22-tetraene-24-carboxylic acid ethyl ester [Formula (VI): $R^3$=α-$CH_3$, $R^4$=(i-Pr)$_3$Si, $R^5$=H, $R^9$=$CH_2CH_3$, Y=CH=CH]

The aldehyde from Preparation 4 (120 mg) and carboethoxymethylene triphenylphosphorane (4 equivalents) in dimethylsulphoxide were stirred at 105° for 5 hours, whereafter the mixture was cooled, diluted with ethyl acetate and washed, and the solvents were removed. The resulting product was purified by chromatography to give the title compound (95 mg): IR (CDCl$_3$) $\upsilon_{max}$ 1595, 1635, 1695 cm$^{-1}$; NMR (CDCl$_3$) δ 0.7 (s, 18-H's), 3.8–4.3 (q, —O—CH of ethyl), 5.3–5.8, 7.2–7.7 (m, side chain —CH=CH's), 6.3–7.2 (m, 1-, 2- and 4-H's).

b) 3-Triisopropylsilyloxy-24,24-bispropargyl-19-nor-chol-1,3,5(10),22-tetraen-24-ol [Formula (I): $R^1$=$R^2$=$CH_2C\equiv CH$, $R^3$=α-$CH_3$, $R^4$=(i-Pr)$_3$Si, $R^5$=H, X=OH, Y=CH=CH]

Propargyl aluminum reagent as prepared as in Example 3(b) (0.7 ml, 5 equivalents) was added dropwise to the ethyl ester from (a) above (55 mg) in tetrahydrofuran (1 ml). The resulting mixture was stirred for 1 hour and then worked up. The product was purified by PTLC to give the title compound (45 mg): IR (CDCl$_3$) $\upsilon_{max}$ 1600, 3280, 3500–3600 cm$^{-1}$; NMR (CDCl$_3$) δ 0.7 (s, 18-H's), 5.4–5.7 (m, side chain —CH=CH's), 6.3–7.3 (m, 1-, 2- and 4-H's).

c) 3,24-Dihydroxy-24,24-bispropargyl-19-nor-chol-1,3,5(10),22-tetraene [Formula (I): $R^1$=$R^2$=$CH_2C\equiv CH$, $R^3$=α-$CH_3$, $R^4$=$R^5$=H, X=OH, Y=CH=CH The silyl ether from (b) above (45 mg) was desilylated by treatment with tetrabutylammonium fluoride (0.3 ml) in tetrahydrofuran (0.3 ml) at room temperature overnight. The product was purified by PTLC to give the title compound (25 mg): IR (CDCl$_3$) $\upsilon_{max}$ 1580, 1600, 3280, 3520–3620 cm$^{-1}$; NMR (CDCl$_3$) δ 0.71 (s, 18-H's), 5.4–5.7 (bm, side chain —CH=CH's), 6.3–7.3 (m, 1-, 2- and 4-H's).

d) 2-Methoxy-3,24-dihydroxy-24,24-bispropargyl-19-nor-chol-1,3,5(10),22-tetraene [Formula (I): $R^1$=$R^2$=$CH_2C\equiv CH$, $R^3$=α-$CH_3$, $R^4$=H, $R^5$=OCH$_3$, X=OH, Y=Ch=CH]

This is prepared from the product of Preparation 6(e) by following the procedures of steps (a)–(c) above.

e) 3,24-Dihydroxy-20-epi-24,24-bispropargyl-19-nor-chol-1,3,5(10),22-tetraene [Formula (I): $R^1$=$R^2$=$CH_2C\equiv CH$, $R^3$=β-$CH_3$, $R^4$=$R^5$=H, X=OH, Y=CH=CH]

This is prepared from the product of Preparation 8(h) by following the procedures of steps (a)–(c) above.

EXAMPLE 5 a) 3-Hydroxy-25-amino-26,27-bishomo-19-nor-cholest-1,3,5(10)-trien-23-yne [Formula (I): $R^1$=$R^2$=$CH_2CH_3$, $R^3$=α-$CH_3$, $R^4$=$R^5$=H, X=NH$_2$, Y=$CH_2$—C≡C]

Butyl lithium (3.8 ml, 6.1 mmol) was added dropwise to a solution of 1,1-diethylpropargylamine (800 mg) in hexane (20 ml) at 0°. The resulting mixture was stirred for 30 minutes, brought to room temperature, stirred for a further 1.5 hours, and then cooled to 0°. A solution of the 20-bromomethyl compound from Preparation 3(d) (300 mg) in hexane (4 ml) was added dropwise, whereafter the solution was stirred for 30 minutes, warmed to 40° and then stirred for 24 hours. The reaction was quenched with ammonium chloride and the product was extracted into ether. The extract was washed, dried and purified by chromatography to give the title compound (110 mg): IR (CDCl$_3$) $\upsilon_{max}$ 1580, 1600, 3000–3640 cm$^{-1}$; NMR (CDCl$_3$) δ 0.7 (s, 18-H's), 6.3–7.3 (m, 1-, 2- and 4-H's).

b) 2-Methoxy-3-hydroxy-25-amino-26,27-bishomo-19-nor-cholest-1,3,5(10)-trien-23-yne [Formula (I): $R^1$=$R^2$=$CH_2CH_3$, $R^3$=α-$CH_3$, $R^4$=H, $R^5$=OCH$_3$, X=NH$_2$, Y=$CH_2$C≡C]

This is prepared from the product of Preparation 6(f) by following the procedure of step (a) above.

c) 3-Hydroxy-20-epi-25-amino-26,27-bishomo-19-nor-cholest-1,3,5(10)-trien-23-yne [Formula (I): =$R^2$=$CH_2CH_3$, $R^3$=β-$CH_3$, $R^4$=$R^5$=H, X=NH$_2$, Y=$CH_2$C≡C This is prepared from the product of Preparation 8(i) by following the procedure of step (a) above.

EXAMPLE 6 a) 3-Hydroxy-25-amino-26,27-bishomo-19-nor-cholest-1,3,5(10)-triene [Formula (I): $R^1$=$R^2$=—CH$_2$CH$_3$, $R^3$=α-$CH_3$, $R^4$=$R^5$H, X=NH$_2$, Y=$(CH_2)_3$]

A solution of the amine from Example 5(a) (70 mg) in ethanol (3.5 ml) containing 5% platinum on carbon (15 mg) was stirred overnight under hydrogen. The resulting mixture was filtered, the solvent was removed from the filtrate, and the product was purified by PTLC to give the title compound (18 mg): IR (CDCl$_3$) $\upsilon_{max}$ 1580, 1600, 3000–3640 cm$^{-1}$; NMR (CDCl$_3$) δ 0.67 (s, 18-H's), 6.3–7.3 (m, 1-, 2- and 4-H's).

b) 2-Methoxy-3-hydroxy-25-amino-26,27-bishomo-19-nor-cholesta-1,3,5(10)-triene [Formula (I): $R^1$=$R^2$=$CH_2CH_3$, $R^3$=α-$CH_3$, $R^4$=H, $R^5$=OCH$_3$, X=NH$_2$, Y=$(CH_2)_3$]

This is prepared from the product of Example 5(b) by following the procedure of step (a) above.

c) 3-Hydroxy-20-epi-25-amino-26,26-bishomo-19-nor-cholesta-1,3,5(10)-triene [Formula (I): $R^1$=$R^2$=$CH_2CH_3$, $R^3$=β-$CH_3$, $R^4$=$R^5$=H, X=NH$_2$, Y=$(CH_2)_3$]

This is prepared from the product of Example 5(c) by following the procedure of step (a) above.

EXAMPLE 7 a) 3-Hydroxy-25-acetylamino-26,27-bishomo-19-nor-cholest-1,3,5(10)-trien-23-yne [Formula (I): $R^1$=$R^2$=$CH_2CH_3$, $R^3$=α-$CH_3$, $R^4$=$R^5$=H, X=NH(COCH$_3$), Y=$CH_2$—C≡C]

The product from Example 5(a) (10 mg) was treated at room temperature overnight with acetic anhydride (12 mg) in methanol (0.1 ml) containing proton sponge (12 mg). The reaction mixture was worked up and the product was purified by PTLC to give the title compound (10 mg): NMR (CDCl$_3$) δ 0.67 (s, 18-H's),1.86 (s, NHCOCH's), 6.3–7.3 (m, 1-, 2- and 4-H's).

b) 2-Methoxy-3-hydroxy-25-acetylamino-26,27-bishomo-19-nor-cholest-1,3,5(10)-trien-23-yne [Formula (I): R$^1$=R$^2$=CH$_2$CH$_3$, R$^3$=α-CH$_3$, R$^4$=H, R$^5$=OCH$_3$, X=NH(COCH$_3$), Y=CH$_2$—C≡C]

This is prepared from the product of Example 5(b) by following the procedure of step (a) above.

c) 3-Hydroxy-20-epi-25-acetylamino-26,27-bishomo-19-nor-cholest-1,3,5(10)-trien-23-yne [Formula (I): R$^1$=R$^2$=CH$_2$CH$_3$, R$^3$=α-CH$_3$, R$^4$=R$^5$=H, X=NH(COCH$_3$), Y=CH$_2$—C≡C]

This is prepared from the product of Example 5(c) following the procedure of step (a) above.

EXAMPLE 8 a) 3-Triisopropylsilyloxy-22-hydroxy-25-amino-26,27-bishomo-19-nor-cholest-1,3,5(10)-trien-23-yne [Formula (I): R$^1$=R$^2$=CH$_2$CH$_3$, R$^3$=α-CH$_3$, R$^4$=(i-Pr)$_3$Si, R$^5$=H, X=NH$_2$, Y=CH(OH)—C≡C]

The 20-formyl compound from Preparation 4 (200 mg) in tetrahydrofuran (1 ml) was added at −78° to a solution of the anion prepared from 1,1-diethylpropargylamine (400 mg) and butyl lithium (1.9 ml, 3 mmol) as in Example 5(a). The resulting mixture was stirred at −78° for 30 minutes, quenched with ammonium acetate, brought to room temperature and worked up. The product was purified by chromatography to give the title compound (150 mg): NMR (CDCl$_3$) δ 0.7 (s, 18-H's), 4.3–4.6 (bs, 22-HOCH), 6.3–7.3 (m, 1-, 2- and 4-H's).

b) 3,22-Dihydroxy-25-amino-26,27-bishomo-19-nor-cholest-1,3,5(10)-trien-23-yne [Formula (I): R$^1$=R$^2$=CH$_2$CH$_3$, R$^3$=αCH$_3$, R$^4$=R$^5$=H, X=NH$_2$, Y=CH(OH)—C≡C]

The silyl compound from (a) above (50 mg) was desilylated by treatment with tetrabutylammonium fluoride (0.3 ml) in tetrahydrofuran (0.3 ml) overnight at room temperature. The resulting mixture was worked up and the product was purified by PTLC to give the title compound: NMR (CDCl$_3$) δ 0.7 (s, 18-H's), 4.3–4.6 (bs, 22-HOCH), 6.3–7.3 (m, 1-, 2- and 4-H's).

c) 2-Methoxy-3,22-dihydroxy-25-amino-26,27-bishomo-19-nor-cholest-1,3,5(10)-trien-23-yne [Formula (I): R$^1$=R$^2$=CH$_2$CH$_3$, R$^3$=α-CH$_3$, R$^4$=H, R$^5$=OCH$_3$, X=NH$_2$, Y=CH(OH)—C≡C]

This is prepared from the product of Preparation 6(e) following the procedures of steps (a) and (b) above.

d) 3,22-Dihydroxy-20-epi-25-amino-26,27-bishomo-19-nor-cholest-1,3,5(10)-trien-23-yne [Formula (I): R$^1$=R$^2$=CH$_2$CH$_3$, =R$^3$=β-CH$_3$, R$^4$=R$^5$=H, X=NH$_2$, Y=CH(OH)—C≡C]

This is prepared from the product of Preparation 8(h) following the procedures of steps (a) and (b) above.

EXAMPLE 9 a) 2-Methoxy-3-triisopropylsilyloxy-23,23a-bishomo-19-nor-chol-1,3,5(10),16-tetraene-24-nitrile [Formula (II): R$^3$=α-CH$_3$, R$^4$=(i-Pr)$_3$Si, R$^5$=OCH$_3$, Y=(CH$_2$)$_4$, Δ16 double bond]

A solution of α-lithio acetonitrile was prepared as follows: acetonitrile (0.32 ml) in tetrahydrofuran (2 ml) was added dropwise at −78° to a solution of butyl lithium (3.75 ml of a 1.6 M solution in hexane) in tetrahydrofuran (4 ml) and the solution stirred for 50 minutes. All but a sixth of the solution (ca 1 mmol) was discarded, whereafter the bromide from Preparation 6(d) (200 mg) in tetrahydrofuran (2 ml) was added dropwise while maintaining the temperature at −78°. The resulting mixture was stirred for 1 hour, allowed to warm to −30°, stirred for a further hour, cooled back to −78°, quenched with ammonium chloride, and worked up. The product was purified by chromatography to give the title compound (145 mg): IR (CDCl$_3$) υ$_{max}$ 1600, 2240 cm$^{-1}$; NMR (CDCl$_3$) δ 0.8 (s, 18-H's), 3.7 (s, OCH's), 5.0–5.3 (bs, 16-H's), 6.34, 6.6 (s, 1,4-H's).

b) 2-Methoxy-3-triisopropylsilyloxy-24-homo-25-amino-19-nor-cholest-1,3,5(10),16-tetraene [Formula (I): R$^1$=R$^2$=CH$_3$, R$^3$=α-CH$_3$, R$^4$=(i-Pr)$_3$Si, R$^5$=OCH$_3$, X=NH$_2$, Y=(CH$_2$)$_4$, Δ16 double bond]

Cerium chloride (384 mg, 1.56 mmol, previously dried at <0.5 mm and 140° for 3 hours) was suspended in tetrahydrofuran (4 ml). This mixture was stirred overnight and then cooled to −78°, whereafter methyl lithium (1.9 mmol, 1.34 ml of a 1.4 M solution in ether) was added dropwise and the mixture was stirred for 15 minutes at −78°, warmed to 0°, stirred for 15 minutes and cooled back to −78°. The nitrile from (a) above (145 mg) in tetrahydrofuran (2 ml) was then added dropwise, and the mixture was stirred for 1.5 hours and then quenched with aqueous ammonium hydroxide. Following work up, removal of the solvent gave the title compound (145 mg): IR (CDCl$_3$) υ$_{max}$ 1600, 3100–3700 cm$^{-1}$; NMR (CDCl$_3$) δ 0.77 (s, 18-H's), 1.3 (s, 26,27-H's), 3.67 (s, OCH's), 5.0–5.3 (bs, 16-H's), 6.4, 6.58 (s, 1,4-H's).

c) 2-Methoxy-3-triisopropylsilyloxy-24-homo-25-acetylamino-19-nor-cholest-1,3,5(10),16-tetraene [Formula (I): R$^1$=R$^2$=CH$_3$, R$^3$=α-CH$_3$, R$^4$=(i-Pr)$_3$Si, R$^5$=OCH$_3$, X=NH(COCH$_3$), Y=(CH$_2$)$_4$, Δ16 double bond]

Acetylation of the amine from (b) above (85 mg) with acetic anhydride (0.425 ml) and pyridine (0.425 ml) in dichloromethane (2 ml) overnight at room temperature gave the title compound (65 mg, purified by PTLC): IR (CDCl$_3$) υ$_{max}$ 1600, 1710, 3420 cm$^{-1}$; NMR (CDCl$_3$) δ 0.77 (s, 18-H's), 1.88 (s, COCH$_3$), 3.7 (s, OCH's), 4.7–5.3 (b, NH', 16-H's), 6.43, 6.6 (s, 1,4-H's).

d) 2-Methoxy-3-hydroxy-24-homo-25-acetylamino-19-nor-cholest-1,3,5(10),16-tetraene [Formula (I): R$^1$=R$^2$=CH$_3$, R$^3$=α-CH$_3$, R$^4$=H, R$^5$=OCH$_3$, X=NH(COCH$_3$), Y=(CH$_2$)$_4$, Δ16 double bond]

The amide from (c) above (65 mg) was desilylated by treatment with tetrabutylammonium fluoride (0.3 ml) in tetrahydrofuran (0.3 ml) for 4 hours, and the crude product was isolated by PTLC to give the title compound (45 mg): IR (CDCl$_3$) υ$_{max}$ 1590, 1710, 3420, 3520 cm$^{-1}$; NMR (CDCl$_3$) δ 0.8 (s, 18-H's), 1.3 (s, 26,27-H's), 1.86 (s, COCH$_3$), 3.78 (s, OCH's), 4.9–5.3 (b, NH, 16H's), 5.3–5.6 (s, OH), 6.47, 6.63 (s, 1,4-H's).

e) 2-Methoxy-3-hydroxy-24-homo-25-amino-19-nor-cholest-1,3,5(10),16-tetraene [Formula (I): R$^1$=R$^2$=CH$_3$, R$^3$=α-CH$_3$, R$^4$=H, R$^5$=OCH$_3$, X=NH$_2$, Y=(CH$_2$)$_4$, Δ16 double bond]

The title compound is obtained by desilylation of the product from (b) above according to the procedure of step (d) above.

f) 2-Methoxy-3-hydroxy-25-acetylamino-19-nor-cholest-1,3,5(10),16-tetraene [Formula (I): $R^1=R^2=CH_3$, $R^3=\alpha\text{—}CH_3$, $R^4=H$, $R^5=OCH_3$, X=NH(COCH$_3$), Y=(CH$_2$)$_3$, $\Delta16$ double bond]

This is prepared by substituting sodium cyanide for the anion in step (a) above and thereafter following the procedures of steps (b)–(d) above.

g) 2-Methoxy-3-hydroxy-25-amino-19-nor-cholest-1,3,5(10),16-tetraene [Formula (I): $R^1=R^2=CH_3$, $R^3=\alpha\text{-}CH_3$, $R^4=H$, $R^5=OCH_3$, $X=NH_2$, Y=(CH$_2$)$_2$, $\Delta16$ double bond]

This is prepared by substituting sodium cyanide for the anion in step (a) above and thereafter following the procedures of steps (b) and (d) above.

EXAMPLE 10 a) Triisopropylsilyloxy-23,23a-bishomo-19-nor-chol-1,3,5(10),6,8,16-hexaene-24-nitrile [Formula (II): $R^3=\alpha\text{-}CH_3$, $R^4=(i\text{-}Pr)_3Si$, $R^5=H$, Y=(CH$_2$)$_4$, $\Delta6$, $\Delta8$ and $\Delta16$ double bonds]

Reaction of the bromide from Preparation 7(e) according to the method of Example 9(a) gave the title compound: IR (CDCl$_3$) $\upsilon_{max}$ 1590, 1610, 2230 cm$^{-1}$; NMR (CDCl$_3$) $\delta$ 0.66 (s, 18-H's), 5.2–5.5 (bs, 16-H's), 6.8–8.0 (m, 1-, 2-, 4-, 6- and 7-H's).

b) 3-Triisopropylsilyloxy-24-homo-25-amino-19-nor-cholest-1,3,5(10),6,8,16-hexaene [Formula (I): $R^1=R^2=CH_3$, $R^3=\alpha\text{-}CH_3$, $R^4=(i\text{-}Pr)_3Si$, $R^5H$, X=NH$_2$, Y=(CH$_2$)$_4$, $\Delta6$, $\Delta8$ and $\Delta16$ double bonds]

The title compound was prepared by reaction of the nitrile from (a) above as in Example 9(b).

c) 3-Triisopropylsilyloxy-24-homo-25-acetylamino-19-nor-cholest-1,3,5(10),6,8,16-hexaene [Formula (I): $R^1=R^2=CH_3$, $R^3=\alpha\text{-}CH_3$, $R^4=(i\text{-}Pr)_3Si$, $R^5=H$, X=NH(COCH$_3$), Y=(CH$_2$)$_4$, $\Delta6$, $\Delta8$ and $\Delta16$ double bonds]

Acetylation of the amine from (b) above as in Example 9(c) gave the title compound (45 mg): IR (CDCl$_3$) $\upsilon_{max}$ 1595, 1605, 1670, 3420 cm$^{-1}$; NMR (CDCl$_3$) $\delta$ 0.67 (s, 18-H's), 1.3 (s, 26,27-H's), 1.87 (s, COCH$_3$), 4.7–5.1 (b, NH), 5.1–5.4 (b, 16-H) 6.7–8.0 (s, 1-, 2-, 4-, 6- and 7-H's).

d) 3-Hydroxy-24-homo-25-acetylamino-19-nor-cholest-1,3,5(10),6,8,16-hexaene [Formula (I): $R^1=R^2=CH_3$, $R^3=\alpha\text{-}CH_3$, $R^4=R^5=H$, X=NH(COCH$_3$), Y=(CH$_2$)$_4$, $\Delta6$, $\Delta8$ and $\Delta16$ double bonds]

The amide from (c) above (45 mg) was desilylated by treatment with tetrabutylammonium fluoride (0.25 ml) in tetrahydrofuran (0.25 ml) at room temperature overnight to give the title compound (28 mg, isolated by PTLC): IR (CDCl$_3$) $\upsilon_{max}$ 1590, 1610, 1650, 3440 cm$^{-1}$; NMR (CDCl$_3$) $\delta$ 0.67 (s, 18-H's), 1.0 (d, 21-H's), 1.27 (s, 26,27-H's), 1.88 (s, COCH$_3$), 4.8–5.4 (b, NH, 16-H), 6.7–8.0 (m, 1-, 2-, 4-, 6- and 7-H's).

e) 3-Hydroxy-24-homo-25-amino-19-nor-cholest-1,3,5(10),6,8,16-hexaene [Formula (I) $R^1=R^2=CH_3$, $R^3=\alpha\text{-}CH_3$, $R^4=R^5=H$, $X=NH_2$, Y=(CH$_2$)$_4$, $\Delta6$, $\Delta8$ and $\Delta16$ double bonds]

The title compound is obtained by desilylation of the product from (b) above according to the procedure of (d) above.

EXAMPLE 11 a) 3-Triisopropylsilyloxy-25-triethylsilyloxy-19-nor-cholest-1,3,5(10)-trien-23-yne [Formula (I): $R^1=R^2=CH_3$, $R^3=\alpha\text{-}CH_3$, $R^4=(i\text{-}Pr)_3Si$, $R^5=H$, X=OSi(CH$_2$CH$_3$)$_3$, Y=CH$_2$C≡C]

Butyl lithium (2.5 ml, 4 mmol) was added dropwise to a solution of [(1,1-dimethyl-2-propynyl)oxy]triethylsilane (792 mg) in hexane containing hexamethylphosphoramide (0.8 ml) at 0°. The resulting mixture was stirred for 30 minutes at that temperature and for a further 1.5 hours at room temperature, and was then cooled again to 0°, whereafter a solution of the bromide from Preparation 3(d) (210 mg) in hexane (4 ml) was added dropwise. The mixture was stirred for 30 minutes at 0°, 2 hours at room temperature, and overnight at 45° C. The reaction was quenched with ammonium chloride and worked up. Chromatography gave a mixture of the 25-desilylated analogue (15 mg, see below) and the title compound (210 mg): NMR (CDCl$_3$) $\delta$ 0.72 (s, 18-H's), 1.48 (s, 26,27-H's, some at 1.42 for the silylated compound), 6.3–7.3 (1-, 2- and 4-H's).

b) 3,25-Dihydroxy-19-nor-cholest-1,3,5(10)-trien-23-yne [Formula (I), $R^1=R^2=CH_3$, $R^3=\alpha\text{-}CH_3$, $R^4=R^5=H$, X=OH, Y=CH$_2$C≡C]

The product from (a) above was desilylated as in Example 1(d) and purified by PTLC to give the title compound (50 mg, insoluble and difficult to manipulate): IR (CDCl$_3$) $\upsilon_{max}$ 1600, 3480 cm$^{-1}$.

c) 3,25-Dihydroxy-19-nor-cholest-1,3,5(10)-triene [Formula (I), $R^1=R^2=CH_3$, $R^3=\alpha\text{-}CH_3$, $R^4=R^5=H$, X=OH, Y=(CH$_2$)$_3$]

A solution of the product from (b) above (40 mg) in ethyl acetate (16 ml) containing palladium (5% on carbon, 10 mg) was stirred overnight under hydrogen. The reaction mixture was worked up and the product was purified by PTLC to give the title compound (28 mg): NMR (CDCl$_3$) $\delta$ 0.7 (s, 18-H's), 1.18 (s, 26,27-H's), 6.2, 7.3 (m, 1-, 2- and 4-H's).

d) 2-Methoxy-3,25-dihydroxy-19-nor-cholest-1,3,5(10)-trien-23-yne [Formula (I): $R^1=R^2=CH_3$, $R^3=\alpha\text{-}CH_3$, $R^4=H$, $R^5=OCH_3$, X=OH, Y=CH$_2$C≡C]

This is prepared from the product of Preparation 6(f) by following the procedures of the above steps (a) and (b).

e) 3,25-Dihydroxy-20-epi-19-nor-cholest-1,3,5(10)-trien-23-yne [Formula (I): $R^1=R^2=CH_3$, $R^3=\beta\text{-}CH_3$, $R^4=R^5=H$, X=OH, Y=CH$_2$C≡C]

This is prepared from the product of Preparation 8(i) by following the procedures of the above steps (a) and (b).

f) 2-Methoxy-3,25-dihydroxy-19-nor-cholest-1,3,5(10)-triene [Formula (I): $R^1=R^2=CH_3$, $R^3=\alpha\text{-}CH_3$, $R^4=H$, $R^5=OCH_3$, X=OH, Y=(CH$_2$)$_3$]

This is prepared by hydrogenation of the product from (d) above as in step (c) above.

g) 3,25-Dihydroxy-20-epi-19-nor-cholest-1,3,5(10)-triene [Formula (I): $R^1=R^2=CH_3$, $R^3=\beta\text{-}CH_3$, $R^4=R^5=H$, X=OH, Y=(CH$_2$)$_3$]

This is prepared by hydrogenation of the product from (e) above as in step (c) above.

EXAMPLE 12 a) 3-Triisopropylsilyloxy-24,24a-bishomo-19-nor-chol-1,3,5(10),22,24(24a)pentaene-24b-carboxylic acid ethyl ester [Formula (VI): $R^3=\alpha\text{-}CH_3$, $R^4=(i\text{-}Pr)_3Si$, $R^5=H$, $R^9=CH_2CH_3$, Y=CH=CH—CH=CH]

The aldehyde from Preparation 4(b) (150 mg) was stirred at 105° for 4 hours in dimethylsulphoxide (3 ml) containing the ylid prepared by washing a solution of ethyl-4-bromotrimethylphosphonium butenoate (364 mg) in dichloromethane with 2N sodium hydroxide and removing the solvents. The reaction mixture was worked up and the product was purified to give the 3-OH analogue of the title compound (40 mg) and the title compound (100 mg): IR (CDCl$_3$) $\upsilon_{max}$ 1600, 1630, 1690 cm$^{-1}$; NMR (CDCl$_3$) δ 0.73 (s, 18-H's), 3.8–4.4 (q, —O—CH of ethyl), 5.3–5.8, 6.3–7.7 (m, side chain —CH=CH's, 1-, 2- and 4-H's).

b) 3-Triisopropylsilyloxy-25-hydroxy-24,24a-bishomo-19-nor-cholest-1,3,5(10),22,24 (24a)-pentaene [Formula (I): R$^1$=R$^2$=CH$_3$, R$^3$=α-CH$_3$, R$^4$=(i-Pr)$_3$Si—, R$^5$=H, X=OH, Y=CH=CH—CH=CH]

Methyl lithium (0.36 ml, 5 equivalents) was added dropwise to a solution of the ester from (a) above (58 mg) in tetrahydrofuran (4 ml) at −45°, and the resulting mixture was stirred for 30 minutes, then quenched and worked up. The product was purified by PTLC to give the title compound (27 mg): IR (CDCl$_3$) $\upsilon_{max}$ 1596, 3650 cm$^{-1}$; NMR (CDCl$_3$) δ 0.7 (s, 18-H's), 1.32 (s, 26,27-H's), 5.2–6.2 (22-, 23-, 24- and 24a-H's), 6.2–7.4 (m, 1-, 2- and 4-H's).

c) 3,25-Dihydroxy-24,24a-bishomo-19-nor-cholest-1,3,5(10),22,24(24a)-pentaene [Formula (I): R$^1$=R$^2$=CH$_3$, R$^3$=α-CH$_3$, R$^4$=R$^5$=H, X=OH, Y=CH=CH—CH=CH]

The silyl ether from (b) above (27 mg) was desilylated as in Example 1(d) and purified by PTLC to give title compound (18 mg): NMR (CDCl$_3$/CD$_3$OH) δ 0.72 (s, 18-H's), 1.3 (s, 26,27-H's), 5.1–6.3 (22-, 23-, 24- and 24a-H's), 6.3–7.4 (m, 1-, 2- and 4-H's).

EXAMPLE 13 a) 3-Triisopropylsilyloxy-20-epi-23,23a-bishomo-19-nor-chol-1,3,5(10),16-tetraene-24-nitrile [Formula (II): R$^3$=β-CH$_3$, R$^4$=(i-Pr)$_3$Si, R$^5$=H, Y=(CH$_2$)$_4$, Δ16 double bond]

Treatment of the bromide from Preparation 8(g) (350 mg) with the lithium salt of acetonitrile according to the procedure of Example 3(a) gave the title compound: IR $\upsilon_{max}$ 2250, 1610, 1450–1600 (3 bands) cm$^{-1}$; NMR (CDCl$_3$) δ 0.78 (s, 18-H's), 5.2 (bs, 16-H), 6.5, 6.95 (m, 1-, 2- and 4-H's).

b) 25-Amino-3-triisopropylsilyloxy-20-epi-24-homo-19-nor-cholest-1,3,5(10),16-tetraene [Formula (I): R$^1$=R$^2$=CH$_3$, R$^3$=β-CH$_3$, R$^4$=(i-Pr)$_3$Si—, R$^5$=H, X=NH$_2$, Y=—(CH$_2$)$_4$, Δ16 double bond]

The nitrite from (a) above was treated with cerium chloride/methyl lithium according to the procedure of Example 3(b) to give the title compound (100 mg): IR (CDCl$_3$) $\upsilon_{max}$ 1610, 1450–1600 (3 bands) cm$^{-1}$; NMR (CDCl$_3$) δ 0.78 (s, 18-H's), 1.2 (26,27-H's), 5.2 (bs, 16-H), 6.5, 6.95 (m, 1-, 2- and 4-H's).

c) 25-Amino-3-hydroxy-20-epi-24-homo-19-nor-cholest-1,3,5(10),16-tetraene [Formula (I): R$^1$=R$^2$=CH$_3$, R$^3$=β-CH$_3$, R$^4$=R$^5$=H, X=NH$_2$, Y=(CH$_2$)$_4$—, Δ16 double bond]

The silyl ether from (b) above (40 mg) was desilyated as in Example 1(d) to give the title compound: IR (CDCl$_3$) $\upsilon_{max}$ 3600, 1615, 1450–1600 (2 bands) cm$^{-1}$; NMR (CDCl$_3$) δ 0.78 (s, 18-H's), 1.05 (d, 21-H's), 1.2 (26,27-H's), 3.9 (bs, 3H [exchanges with D$_2$O]—OH, NH's), 5.2 (bs, 16-H), 6.5, 6.95 (m, 1-, 2- and 4-H's).

d) 25-Acetylmino-3-triisopropylsilyoxy-20-epi-24-homo-19-nor-cholest-1,3,5(10),16-tetraene [Formula (I): R$^1$=R$^2$=CH$_3$, R$^3$=β-H$_3$, R$^4$=(i-Pr)$_3$Si, R$^5$=H, X=NH(COCH$_3$), Y=(CH$_2$)$_4$—, Δ16 double bond]

The silyl ether from (b) above (60 mg) was acetylated as in Example 3(c) to give the title compound: IR (CDCl$_3$) $\upsilon_{max}$ 3420, 1660, 1610, 1450–1600 (2 bands) cm$^{-1}$; NMR (CDCl$_3$) δ 0.78 (s, 18-H's), 1.2 (26,27-H's), 1.9 (bs, NH), 5.2 (bs, 16-H), 6.5, 6.95 (m, 1-, 2- and 4-H's).

e) 25-Acetylamino-3-hydroxy-20-epi-24-homo-19-nor-cholest-1,3,5(10),16-tetraene [Formula (I); R$^1$=R$^2$=CH$_3$, R$^3$=β-CH$_3$, R$^4$=R$^5$=H, X=NH(COCH$_3$), Y=—(CH$_2$)$_4$—, Δ16 double bond]

The silyl either from (d) above (60 mg) was desilyated as in Example 1(d) to give the title compound (36 mg): IR $\upsilon_{max}$ 3420, 1610, 1665, 1450–1600 (2 bands) cm$^{-1}$; NMR (CDCl$_3$) δ 0.78 (s, 18-H's), 1.2 (26,27-H's), 1.9 (bs, NH), 5.2 (bs, 16-H), 6.5, 6.95 (m, 1-, 2- and 4-H's).

f) 25-Amino-3-hydroxy-20-epi-19-nor-cholest-1,3,5 (10),16-tetraene [Formula (I): R$^1$=R$^2$=CH$_3$, R$^3$=β-CH$_3$, R$^4$=R$^5$=H, X=NH$_2$, Y=(CH$_2$)$_3$, Δ16 double bond]

This is prepared by substituting sodium cyanide for the anion in step (a) above and thereafter following the procedures of steps (b) and (c) above.

g) 25-Acetylamino-3-hydroxy-20-epi-19-nor-cholest-1,3,5(10),16-tetraene [Formula (I): R$^1$=R$^2$=CH$_3$, R$^3$=β-CH$_3$, R$^4$=R$^5$=H, X=NH(COCH$_3$), Y=(CH$_2$)$_3$, Δ16 double bond This is prepared by substituting sodium cyanide for the anion in step (a) above and thereafter following the procedures of steps (b), (d) and (e) above.

EXAMPLE 14 a) 3-Triisopropylsilyloxy-23,23a-bishomo-19-nor-chol-1,3,5(10),6,16-pentaen-24-nitrile [Formula (II): R$^3$=α-CH$_3$, R$^4$=(i-Pr)$_3$Si, R$^5$=H, Y=(CH$_2$)$_4$, Δ6 and Δ16 double bonds]

Reaction of the bromide from Preparation 9(e) in accordance with the procedure of Example 9(a) gave the title compound: IR (CDCl$_3$) $\upsilon_{max}$ 1590, 1615, 2240 cm$^{-1}$; NMR (CDCl$_3$) δ 0.67 (s, 18-H's), 5.2–5.5 (b, 16-H's), 6.7–8.0 (m, 1-, 2- and 4-H's).

b) 3-Triisopropylsilyloxy-24-homo-25-amino-19-nor-cholest-1,3,5(10),6,16-pentaene [Formula (I): R$^1$=R$^2$=CH$_3$, R$^3$=α-CH$_3$, R$^4$=(i-Pr)$_3$Si, R$^5$=H, X=NH$_3$, Y=(CH$_2$)$_4$, Δ6 and Δ16 double bonds]

The title compound was prepared from the nitrile from (a) above as in Example 9(b).

c) 3-Triisopropylsilyloxy-24-homo-25-acetylamino-19-nor-cholest-1,3,5(10),6,16-pentaene [Formula (I) : R$^1$=R$^2$=CH$_3$, R$^3$=α-CH$_3$, R$^4$=(i-Pr)$_3$Si, R$^5$=H, X=NH(COCH$_3$), Y=(CH$_2$)$_4$, Δ6 and Δ16 double bonds]

Acetylation of the amine from (b) above as in Example 9(c) gave the title compound (60 mg): IR (CDCl$_3$) $\upsilon_{max}$ 1590, 1615, 1660, 3420 cm$^{-1}$; NMR (CDCl$_3$) δ 0.67 (s, 18-H's), 1.26 (s, 26,27-H's), 1.87 (s, COCH$_3$), 4.9–5.2 (b, NH), 5.2–5.5 (b, 16-H), 6.7–9.0 (s, 1-, 2-, 4- and 6-H's).

d) 3-Hydroxy-24-homo-25-acetylamino-19-nor-cholest-1,3,5(10),6,16-pentaene [Formula (I): R$^1$=R$^2$=CH$_3$, R$^3$=α-CH$_3$, R$^4$=H, R$^5$=H, X=NH(COCH$_3$), Y=(CH$_2$)$_4$, Δ6 and Δ16 double bonds]

The amide from (c) above (50 mg) was desilyated by treatment with tetrabutylammonium fluoride (0.3 ml) in tetrahydrofuran (0.35 ml) at room temperature for 4 hours to give the title compound (36 mg, isolated by PTLC): IR (CDCl$_3$) υ$_{max}$ 1590, 1610, 1650, 3440–3640 cm$^{-1}$; NMR (CDCl$_3$) δ 0.63 (s, 18-H's), 1.3 (s, 26,27-H's), 5.0–5.5 (b, NH, 16-H), 6.7–8.0 (m, 1,2-H's).

e) 3-Hydroxy-24-homo-25-amino-19-nor-cholest-1,3,5(10),6,16-pentaene [Formula (I): R$^1$=R$^2$=CH$_3$, R$^3$=α-CH$_3$, R$^4$=H, R$^5$=H, X=NH$_2$, Y=(CH$_2$)$_4$, Δ6 and Δ16 double bonds]

The title compound is obtained by desilyation of the product from step (b) above by the procedure of step (d) above.

What is claimed is:

1. Compounds of formula (I)

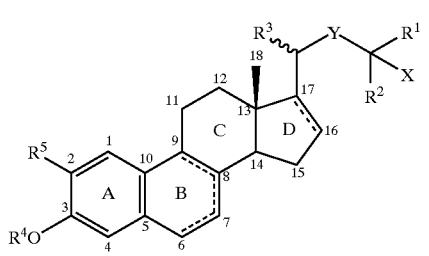

in which:
R$^1$ and R$^2$, which may be the same or different, each represents a lower alkyl, alkenyl or alkynyl group;
R$^3$ represents a methyl group having α- or β-configuration;
R$^4$ represents a hydrogen atom or an etherifying or esterifying group;
R$^5$ represents a hydrogen atom, a hydroxyl group or a lower alkoxy group;
X represents a group OR$^4$, wherein R$^4$ is as defined above, or a group NR$^6$R$^7$ wherein R$^6$ represents a hydrogen atom, an aliphatic or araliphatic organic group, or an acyl group comprising an aliphatic, araliphatic or aryl organic group linked to the nitrogen atom by way of a carbonyl group; and R$^7$ is a hydrogen atom or a lower alkyl group;
Y represents a lower alkylene, alkenylene or alkynylene group optionally substituted by a hydroxyl, etherified hydroxyl or esterified hydroxyl group; and
the dotted lines signify that double bonds may be present at the 16(17)-position and/or either at the 6(7)- and 8(9)-positions or at the 7(8)-position.

2. Compounds of formula (I) as claimed in claim 1 wherein R$^1$ and R$^2$ are independently selected from C$_{1-6}$ alkyl groups and C$_{2-7}$ alkenyl and alkynyl groups.

3. Compounds of formula (I) as claimed in claim 2 wherein R$^1$ and R$^2$ are straight chain groups.

4. Compounds of formula (I) as claimed in claim 2 wherein R$^1$ and R$^2$ are selected from methyl, ethyl and propargyl groups.

5. Compounds of formula (I) as claimed in claim 1 wherein R$^4$ a hydrogen atom, a silyl group, a C$_{1-6}$ alkyl group optionally interrupted by one or more oxygen atoms or substituted by a lower cycloalkyl group, a cyclic ether group, a C$_{1-6}$ alkanoyl group, an aroyl group, a C$_{1-6}$ alkane sulphonyl or halogenated methane sulphonyl group, or an arene sulphonyl group.

6. Compounds of formula (I) as claimed in claim 5 wherein R$^4$ is a hydrogen atom.

7. Compounds of formula (I) as claimed in claim 5 wherein R$^4$ is a metabolically labile group or a lower alkyl group.

8. Compounds of formula (I) as claimed in claim 1 wherein R$^5$ represents a hydrogen atom or a methoxy group.

9. Compounds of formula (I) as claimed in claim 1 wherein X represents a hydroxyl group or a group of formula NR$^6$R$^7$ wherein:

R$^6$ is a C$_{1-6}$ alkyl group, C$_{6-12}$ carbocyclic aryl C$_{1-4}$ alkyl group, C$_{1-6}$ alkanoyl group, C$_{6-12}$ carbocyclic aryl C$_{2-5}$ alkanoyl group, C$_{7-13}$ carbocyclic aroyl group or any of the preceding groups substituted by one or more halo, C$_{1-4}$ alkyl, C$_{1-4}$ alkoxy, C$_{1-4}$ alkanoyl, C$_{1-4}$ alkylamino, di (C$_{1-4}$ alkyl)amino, nitro, carbamoyl or C$_{1-4}$ alkanoylamino substituents; and R$^7$ is a hydrogen atom or a C1–6 alkyl group.

10. Compounds of formula (I) as claimed in claim 9 wherein X represents a hydroxyl, amino, methylamino, ethylamino, N-ethyl-N-methylamino, acetylamino, benzamido or phenylacetylamino group.

11. Compounds of formula (I) as claimed in claim 1 wherein Y contains up to 7 carbon atoms and up to 3 multiple bonds.

12. Compounds of formula (I) as claimed in claim 11 wherein Y is a straight chain C$_{2-6}$ group.

13. Compounds of formula (I) as claimed in claim 1 wherein Y is substituted by a hydroxyl, etherified hydroxyl or esterified hydroxyl group positioned α-, β- or γ- to the group —C(R$^1$)(R$^2$), X or α- to any triple bond present in the group Y.

14. Compounds as claimed in claim 11 wherein Y is selected from ethylene, trimethylene, tetramethylene, vinylene, buta-1,3-dienylene, prop-2-ynylene and 1-hydroxyprop-2-ynylene.

15. Compounds of formula (I) as claimed in claim 1 wherein:
R$^1$ and R$^2$, which may be the same or different, each represents a lower alkyl group;
R$^5$ represents a hydrogen atom; and
X represents a group NR$^6$R$^7$ wherein R$^7$ is hydrogen.

16. The compounds:
25-acetylamino-3-hydroxy-24-homo-19-nor-cholest-1,3,5(10),16-tetraene;
25-ethylamino-3-hydroxy-24-homo-19-nor-cholest-1,3,5(10),16-tetraene;
25-methylamino-3-hydroxy-24-homo-19-nor-cholest-1,3,5(10),16-tetraene;
25-dimethylamino-3-hydroxy-24-homo-19-nor-cholest-1,3,5(10),16-tetraene;
25-(N-ethyl-N-methylamino)-3-hydroxy-24-homo-19-nor-cholest-1,3,5(10),16-tetraene;
25-acetylamino-3-methoxy-24-homo-19-nor-cholest-1,3,5(10),16-tetraene;
25-acetylamino-3-ethoxy-24-homo-19-nor-cholest-1,3,5(10),16-tetraene;
25-acetylamino-3-isobutoxy-24-homo-19-nor-cholest-1,3,5(10),16-tetraene;

25-benzamido-3-hydroxy-24-homo-19-nor-cholest-1,3,5(10),16-tetraene;
25-phenylacetylamino-3-hydroxy-24-homo-19-nor-cholest-1,3,5(10),16-tetraene;
25-acetylamino-3-hydroxy-24-homo-19-nor-cholest-1,3,5(10)-triene;
3,24-dihydroxy-24-propargyl-19–26,27-trisnor-cholest-1,3,5(10)-triene;
2-methoxy-3,24-dihydroxy-24-propargyl-19,26,27-trisnor-cholesta-1,3,5(10)-triene;
3,24-dihydroxy-20-epi-24-propargyl-19,26,27-trisnor-cholest-1,3,5(10)-triene;
3,24-dihydroxy-24,24-bispropargyl-19-nor-chol-1,3,5(10),22-tetraene;
2-methoxy-3,24-dihydroxy-24,24-bispropargyl-19-nor-chol-1,3,5(10),22-tetraene;
3,24-dihydroxy-20-epi-24,24-bispropargyl-19-nor-chol-1,3,5(10),22-tetraene;
3-hydroxy-25-amino-26,27-bishomo-19-nor-cholest-1,3,5(10)-trien-23-yne;
2-methoxy-3-hydroxy-25-amino-26,27-bishomo-19-nor-cholest-1,3,5(10)-trien-23-yne;
3-hydroxy-20-epi-25-amino-26,27-bishomo-19-nor-cholest-1,3,5(10)-trien-23-yne;
3-hydroxy-25-amino-26,27-bishomo-19-nor-cholest-1,3,5(10)-triene;
2-methoxy-3-hydroxy-25-amino-26,27-bishomo-19-nor-cholesta-1,3,5(10)-triene;
3-hydroxy-20-epi-25-amino-26,26-bishomo-19-nor-cholesta-1,3,5(10)-triene;
3-hydroxy-25-acetylamino-26,27-bishomo-19-nor-cholest-1,3,5(10)-trien-23-yne;
2-methoxy-3-hydroxy-25-acetylamino-26,27-bishomo-19-nor-cholest-1,3,5(10)-trien-23-yne;
3-hydroxy-20-epi-25-acetylamino-26,27-bishomo-19-nor-cholest-1,3,5(10)trien-23-yne;
3,22-dihydroxy-25-amino-26,27-bishomo-19-nor-cholest-1,3,5(10)-trien-23-yne;
2-methoxy-3,22-dihydroxy-25-amino-26,27-bishomo-19-nor-cholest-1,3,5(10)-trien-23-yne;
3,22-dihydroxy-20-epi-25-amino-26,27-bishomo-19-nor-cholest-1,3,5(10)-trien-23-yne;
2-methoxy-3-hydroxy-24-homo-25-acetylamino-19-nor-cholest-1,3,5(10), 16-tetraene;
2-methoxy-3-hydroxy-24-homo-25-amino-19-nor-cholest-1,3,5(10),16-tetraene;
2-methoxy-3-hydroxy-25-acetylamino-19-nor-cholest-1,3,5(10),16-tetraene;
2-methoxy-3-hydroxy-25-amino-19-nor-cholest-1,3,5(10),16-tetraene;
3-hydroxy-24-homo-25-acetylamino-19-nor-cholest-1,3,5(10),6,8,16-hexaene;
3-hydroxy-24-homo-25-amino-19-nor-cholest-1,3,5(10),6,8,16-hexaene;
3,25-dihydroxy-19-nor-cholest-1,3,5(10)-trien-23-yne;
3,25-dihydroxy-19-nor-cholest-1,3,5(10)-triene;
2-methoxy-3,25-dihydroxy-19-nor-cholest-1,3,5(10)-trien-23-yne;
3,25-dihydroxy-20-epi-19-nor-cholest-1,3,5(10)-trien-23-yne;
2-methoxy-3,25-dihydroxy-19-nor-cholest-1,3,5(10)-triene;
3,25-dihydroxy-20-epi-19-nor-cholest-1,3,5(10)-triene;
3,25-dihydroxy-24,24a-bishomo-19-nor-cholest-1,3,5(10),22,24(24a)-pentaene;
25-amino-3-hydroxy-20-epi-24-homo-19-nor-cholest-1,3,5(10),16-tetraene;
25-acetylamino-3-hydroxy-20-epi-19-nor-cholest-1,3,5(10),16-tetraene;
25-amino-3-hydroxy-20-epi-19-nor-cholest-1,3,5(10),16-tetraene;
25-acetylamino-3-hydroxy-20-epi-24-homo-19-nor-cholest-1,3,5(10),16-tetraene;
3-hydroxy-24-homo-25-acetylamino-19-nor-cholest-1,3,5(10),6,16-pentaene; and
3-hydroxy-24-homo-25-amino-19-nor-cholest-1,3,5(10),6,16-pentaene.

17. Pharmaceutical compositions comprising an active compound of formula (I) as claimed in claim 1 in admixture with one or more physiologically acceptable carriers or excipients.

18. A method of treatment of a human or animal subject to promote wound healing comprising administering to said subject a therapeutically effective amount of an active compound of formula (I) as claimed in claim 1.

* * * * *

UNITED STATES PATENT AND TRADEMARK OFFICE
CERTIFICATE OF CORRECTION

PATENT NO. : 6,881,730 B1
APPLICATION NO. : 09/926491
DATED : April 19, 2005
INVENTOR(S) : Robert Henry Hesse et al.

It is certified that error appears in the above-identified patent and that said Letters Patent is hereby corrected as shown below:

On the title page item (22) the filing date of the PCT application should be:

--May 11, 2000--

Signed and Sealed this

Fourth Day of July, 2006

JON W. DUDAS
*Director of the United States Patent and Trademark Office*